(12) United States Patent
Dave et al.

(10) Patent No.: US 8,870,945 B2
(45) Date of Patent: *Oct. 28, 2014

(54) BIOABSORBABLE DEVICE HAVING COMPOSITE STRUCTURE FOR ACCELERATING DEGRADATION

(71) Applicant: Cordis Corporation, Bridgewater, NJ (US)

(72) Inventors: Vipul Dave, Hillsborough, NJ (US); George Landau, Huntingdon Valley, PA (US)

(73) Assignee: Cordis Corporation

( * ) Notice: Subject to any disclaimer, the term of this patent is extended or adjusted under 35 U.S.C. 154(b) by 0 days.

This patent is subject to a terminal disclaimer.

(21) Appl. No.: 13/752,076

(22) Filed: Jan. 28, 2013

(65) Prior Publication Data

US 2013/0144376 A1    Jun. 6, 2013

Related U.S. Application Data

(63) Continuation of application No. 11/539,355, filed on Oct. 6, 2006, now Pat. No. 8,394,488.

(51) Int. Cl.
| | |
|---|---|
| *A61F 2/00* | (2006.01) |
| *B32B 27/32* | (2006.01) |
| *A61F 2/82* | (2013.01) |
| *A61L 31/14* | (2006.01) |
| *A61L 31/06* | (2006.01) |
| *A61L 27/58* | (2006.01) |
| *A61L 27/18* | (2006.01) |

(52) U.S. Cl.
CPC .............. *A61F 2/82* (2013.01); *A61L 31/148* (2013.01); *A61L 31/06* (2013.01); *A61L 27/58* (2013.01); *A61L 27/18* (2013.01)
USPC ........ 623/1.34; 623/1.38; 623/1.42; 428/220; 424/426; 424/422; 424/423

(58) Field of Classification Search
None
See application file for complete search history.

(56) References Cited

U.S. PATENT DOCUMENTS

| | | |
|---|---|---|
| 5,290,271 A | 3/1994 | Jernberg |
| 5,322,691 A | 6/1994 | Darougar et al. |

(Continued)

FOREIGN PATENT DOCUMENTS

| | | |
|---|---|---|
| EP | 1600182 A1 | 11/2005 |
| JP | 2001333975 A | 12/2001 |

(Continued)

OTHER PUBLICATIONS

Acuna, V. et al., "Composites of Lactic Acid Polymer and Calcium Phosphate or Calcium Carbonate As Degradable Bone Fillers," Advances in Biomaterials, Elsevier, 1992, Amsterdam, NL, pp. 391-398.

(Continued)

*Primary Examiner* — David Sample
*Assistant Examiner* — Nicole T Gugliotta

(57) ABSTRACT

A medical device has a structure made of a first biodegradable and/or bioabsorbable material and a second biodegradable and/or bioabsorbable material encapsulating a degradation additive incorporated into the first biodegradable and/or bioabsorbable material. The second biodegradable and/or bioabsorbable material has a degradation rate that is faster than the degradation rate of the first biodegradable and/or bioabsorbable material such that the structure experiences a period of accelerated degradation upon release of the degradation additive following sufficient degradation of the second biodegradable and/or bioabsorbable material.

13 Claims, 6 Drawing Sheets

(56) References Cited

U.S. PATENT DOCUMENTS

| | | | |
|---|---|---|---|
| 5,629,077 | A | 5/1997 | Turnland et al. |
| 5,679,723 | A | 10/1997 | Cooper et al. |
| 5,817,328 | A | 10/1998 | Gresser et al. |
| 6,306,166 | B1 | 10/2001 | Barry et al. |
| 6,338,739 | B1 | 1/2002 | Datta et al. |
| 6,419,945 | B1 | 7/2002 | Gresser et al. |
| 6,423,092 | B2 | 7/2002 | Datta et al. |
| 6,544,582 | B1 | 4/2003 | Yoe |
| 6,548,002 | B2 | 4/2003 | Gresser et al. |
| 6,913,765 | B2 | 7/2005 | Li et al. |
| 2004/0028655 | A1* | 2/2004 | Nelson et al. ............... 424/93.2 |
| 2004/0063606 | A1* | 4/2004 | Chu et al. ............... 514/1 |
| 2004/0242722 | A1 | 12/2004 | Rose et al. |
| 2005/0036946 | A1 | 2/2005 | Pathak et al. |
| 2005/0171595 | A1* | 8/2005 | Feldman et al. ............. 623/1.15 |
| 2005/0278015 | A1* | 12/2005 | Dave et al. ............... 623/1.38 |
| 2006/0193892 | A1 | 8/2006 | Furst |
| 2007/0055364 | A1* | 3/2007 | Hossainy et al. ............ 623/1.38 |

FOREIGN PATENT DOCUMENTS

| | | |
|---|---|---|
| WO | 9117789 A | 11/1991 |
| WO | 9619248 A2 | 6/1996 |
| WO | 03026532 A2 | 4/2003 |
| WO | 03030879 A1 | 4/2003 |
| WO | 2004098503 A2 | 11/2004 |
| WO | 2006082221 A1 | 8/2006 |
| WO | 2008011048 A2 | 1/2008 |

OTHER PUBLICATIONS

Agrawal, C.M. et al., "Technique to Control Ph in Vicinity of Biodegrading PLA-PGA Implants," John Wiley & Sons, Inc., CCC 0021-9304197/020105-10., J. Biomed Mater Res (Appl Biomater), 1997, No. 38, pp. 105-114.

Bostman, et al., "Ankle Fractures Treated Using Biodegradable Internal Fixation," Clinical Orthopedic, 1989, No. 238, pp. 195-203.

Bostman et al., "Biodegradable Internal Fixation for Malleolar Fractrures," British Editorial Society of Bone and Joint Surgery, 1987, 69-B(4), pp. 615-619.

Bostman, et al., "Current Concepts Review Absorbable Implants for the Fixation of Fractures," Joint Bone and Joint Surgery, 1991, No. 73, 148-153.

Bostman, et al., "Degradable Polyglycolide Rods for the Internal Fixation of Displaced Bimalleolar Fractures," 1990, International Orthopedic, No. 14, pp. 1-8.

Hirvensalo, et al., "Biodegradable Fixation in Intraarticular Fractures of the Elbow Joint," Acta Orthop., 1988, Scandinavica, Supplementum 227, pp. 78-79.

Hoffmann et al., "Die Distale Radiusfraktur. Frakturstabilisierung Mit Biodegradablen Osteosynthese-8Tiften (Biofix, Die Versorgung Von Sprunggelenlzsfrakturen Unter Verwendung Von Platten Uno Schrauben Aus Resorbserbarem Polymermaterial," Jahrestagung der Deutschen Gesellschaft fur Unfallheilkunde, Nov. 22, 1989, Berlin, No. 92, pp. 430-434 with English Summary.

Li, Suming., "Hydrolytic Degradation Characteristics of Aliphatic Polyesters Derived From Lactic and Glycolic Acids," J. Biomed Mater Res (Appl Biomater), 1999, No. 48, pp. 342-353, John Wiley & Sons, Inc.

Partio et al., "Total Arthroplasties of the Knee in Middle-Finland Central Hospital Between 1977, and 1984," Acta Orthop., 1990, Scandinavica, Supplementum 235 61, No. 1, pp. 43-44.

Rezwan, K., et al., "Biodegradable and Bioactive Porous Polymeriinorganic Composite Scaffolds for Bone Tissue Engineering," Biomaterials, 2006, No. 27, pp. 3413-3431.

Rokkanen, et al., "Biodegradable Implants in Fracture Fixation: Early Results of Treatment of Fractures of the Ankle," Lancet, 1985, No. 1, pp. 1422-1425.

Schiller, C., et al., "Carbonated Calcium Phosphates Are Suitable Ph-8Tabilising Fillers for Biodegradable Polyesters," Elsevier Science Ltd., Biomaterials, 2003, No. 24, pp. 2037-2043.

Schiller, C., et al., "Geometrically Structured Implants for Cranial Reconstruction Made of Biodegradable Polyesters and Calcium Phosphate/Calcium Carbonate," Biomaterials, Elsevier Science Publishers BV, Mar. 2004, Barino, GB, pp. 1239-1247.

Vert, et al., "More About the Degradation of Laiga-Derived Matrices in Aqueous Media," J. Controlled Release, 1991, No. 16, pp. 15-26. BE., 462J/3.962J (Spring 2004).

* cited by examiner

BIOABSORBABLE DEVICE HAVING COMPOSITE STRUCTURE FOR ACCELERATING DEGRADATION

CROSS-REFERENCE TO RELATED APPLICATIONS

This application is a continuation application of Ser. No. 11/539,355 filed Oct. 6, 2006, which is incorporated herein by reference in its entirety.

FIELD AND BACKGROUND OF THE INVENTION

The present invention relates, in general, to implantable medical devices, and, in particular, to new and useful bioabsorbable medical devices that are capable of achieving a desired mass loss through accelerated degradation after the medical device has achieved its desired functional effect or achieved the end of its functional purpose or useful life.

It is widely accepted that polymers have found very relevant and practical uses in the medical field. Thus, the very instability of these polymers, which lead to biodegradation, has proven to be immensely important in medical applications over the last number of decades.

For example, polymers prepared from glycolic acid and lactic acid have found a multitude of uses in the medical industry, beginning with the biodegradable sutures first approved in the 1960's. Since that time, diverse products based on lactic and glycolic acid—and on other materials, including poly(dioxanone), poly(trimethylene carbonate) copolymers, and poly(ε-caprolactone) homopolymers and copolymers—have been accepted for use as medical devices. In addition to these approved devices, a great deal of research continues on polyanhydrides, polyorthoesters, polyphosphazenes, and other biodegradable polymers.

There are a number of reasons as to why a medical practitioner desires a medical device made of a material that degrades. And, the most basic reason begins with the physician's simple desire to have a device that can be used as an implant and will not require a second surgical intervention for removal. Besides eliminating the need for a second surgery, the biodegradation may offer other advantages. For example, a fractured bone that has been fixated with a rigid, nonbiodegradable stainless steel implant has a tendency for refracture upon removal of the implant. Because the stress is borne by the rigid stainless steel, the bone has not been able to carry sufficient load during the healing process.

However, an implant prepared from biodegradable polymer can be engineered to degrade at a rate that will slowly transfer load to the healing bone. Another exciting use for which biodegradable polymers offer tremendous potential is as the basis for drug delivery, either as a drug delivery system alone or in conjunction to functioning as a medical device.

Bioabsorbable implants are typically made from polymeric materials such as lactone-based polyesters. These bulk eroding materials breakdown over time due to chemical hydrolysis to produce water-soluble, low molecular weight fragments. These fragments are then attacked by enzymes to produce lower molecular weight metabolites.

To date, there have been no known bioabsorbable medical devices that are capable of achieving a desired mass loss through accelerated degradation after the medical device has achieved its desired functional effect or achieved the end of its functional purpose or useful life.

SUMMARY OF THE INVENTION

The present invention relates to medical devices that are placed or implanted in the body including medical devices that are placed in vessels such as an artery or a vein or ducts or organs such as the heart. Particularly, the present invention is a medical device that is either made of composite structures comprising biodegradable and/or bioabsorbable material including blends, coatings or layers of biodegradable and/or bioabsorbable material for achieving a desired mass loss through accelerated degradation after the medical device has achieved its desired functional effect or achieved the end of its functional purpose or useful life.

Additionally, the present invention is a medical device that is either made of biodegradable and/or bioabsorbable material including blends, coatings or layers of biodegradable and/or bioabsorbable material and having encapsulated degradation additives conducive for accelerating degradation of the structures or components of the medical device for achieving a desired mass loss through accelerated degradation after the medical device has achieved its desired functional effect or achieved the end of its functional purpose or useful life. In some embodiments, the medical device in accordance with the present invention includes a therapeutic agent released from the medical device as well as other additives such as radiopaque agents and buffering agents.

The present invention is directed to a medical device having a structure made of a first biodegradable and/or bioabsorbable material and a second biodegradable and/or bioabsorbable material. The first biodegradable and/or bioabsorbable material has a degradation rate that is faster than a degradation rate of the second biodegradable and/or bioabsorbable material. And, the structure experiences a period of accelerated degradation upon exposure of the first biodegradable and/or bioabsorbable material.

The present invention is also directed to a medical device having a structure made of one biodegradable and/or bioabsorbable material. A degradation additive is encapsulated by another biodegradable and/or bioabsorbable material forming a nanoparticle or microparticle. The nanoparticle or microparticle is together with the one biodegradable and/or bioabsorbable material of the structure. The other biodegradable and/or bioabsorbable material of the nanoparticle or microparticle has a degradation rate that is faster than a degradation rate of the one biodegradable and/or bioabsorbable material. The structure experiences a period of accelerated degradation upon release of the degradation additive from the nanoparticle or microparticle.

BRIEF DESCRIPTION OF THE DRAWINGS

The novel features of the invention are set forth with particularity in the appended claims. The invention itself, however, both as to organization and methods of operation, together with further objects and advantages thereof, may be understood by reference to the following description, taken in conjunction with the accompanying drawings in which:

DESCRIPTION OF THE PREFERRED EMBODIMENTS

Figure 1:
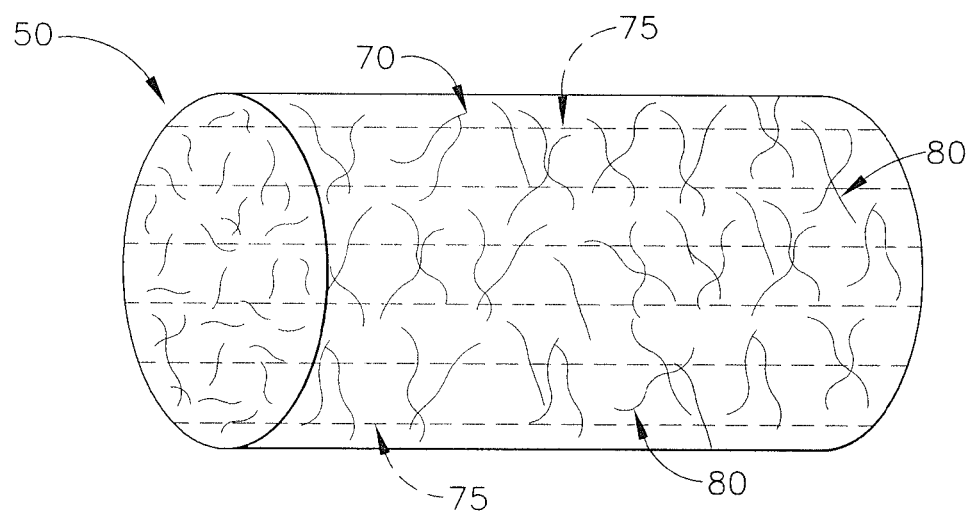
FIG. 1 is a schematic illustration of a medical device having a composite structure of a first biodegradable and/or bioabsorbable material that degrades at a first degradation rate and a second biodegradable and/or bioabsorbable material layered or coated over the first biodegradable and/or bioabsorbable material, wherein the first degradation rate of the first biodegradable and/or bioabsorbable material is faster than the second degradation rate second biodegradable and/or bioabsorbable material in accordance with the present invention.
Figure 2:
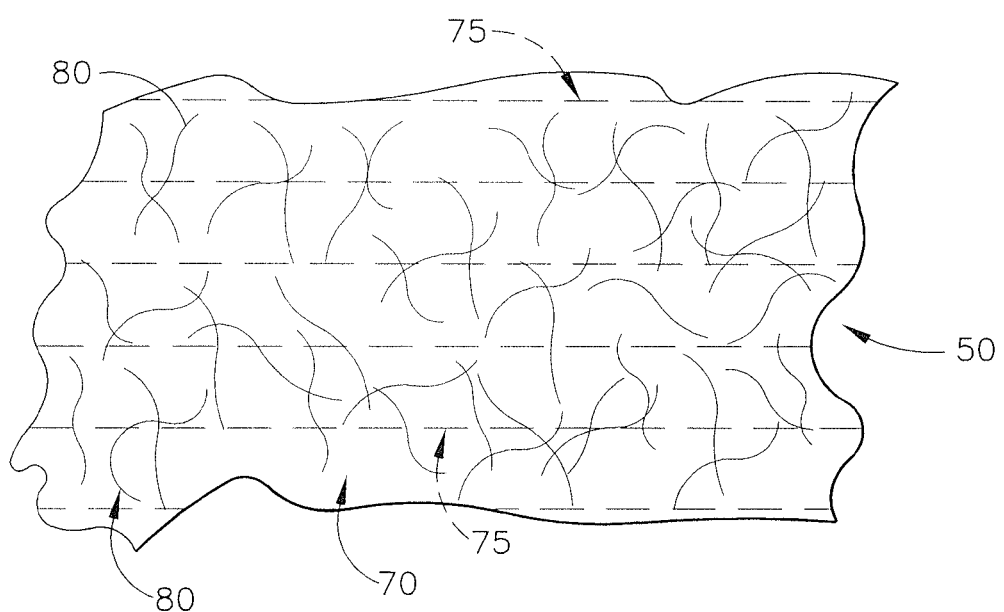
FIG. 2 is a schematic illustration of a portion of structure of the medical device of FIG. 1 in accordance with the present invention.

The present invention relates to medical devices that are placed or implanted in the body including medical devices that are placed in vessels such as an artery or a vein or ducts or organs such as the heart. Particularly, the present invention is a medical device that is either made of composite structures comprising biodegradable and/or bioabsorbable material including blends, coatings or layers of biodegradable and/or bioabsorbable material for achieving a desired mass loss through accelerated degradation after the medical device has achieved its desired functional effect or achieved the end of its functional purpose or useful life.

Additionally, the present invention is a medical device that is either made of biodegradable and/or bioabsorbable material including blends, coatings or layers of biodegradable and/or bioabsorbable material and having encapsulated degradation additives conducive for accelerating degradation of the structures or components of the medical device for achieving a desired mass loss through accelerated degradation after the medical device has achieved its desired functional effect or achieved the end of its functional purpose or useful life. In some embodiments, the medical device in accordance with the present invention includes a therapeutic agent released from the medical device as well as other additives such as radiopaque agents and buffering agents.

As used herein, the terms "biodegradable", "biodegradation", "degradable", "degradation", "degraded", "bioerodible", "erodible" or "erosion" are used interchangeably and are defined as the breaking down or the susceptibility of a material or component to break down or be broken into products, byproducts, components or subcomponents over time such as days, weeks, months or years.

As used herein, the terms "bioabsorbable", "absorbable", "resorbable" and "bioresorbable" are used interchangeably and are defined as the biologic elimination of any of the products of degradation by metabolism and/or excretion.

As used herein, the terms "degradation additive", "selected enzyme", "high pH material", are used interchangeably and defined as any material, agent, compound or substance that accelerates degradation of the structure, components or material of the medical device.

As used herein, the terms "buffering agent", "buffering compound", "buffer", "neutralizing agent", "neutralizing compound", "neutralization agent", or "neutralization compound" are used interchangeably and defined as any material, agent, compound or substance that limits or moderates the rate of change of the pH of a medical device or the local or near environment of the medical devices upon exposure to acid or base.

As used herein, the term "biodegradable material", "biodegradable polymer", "bioabsorbable material", "bioabsorbable polymer", "biomaterial", "biodegradable and/or bioabsorbable material" or "biodegradable and/or bioabsorbable polymer" are used interchangeably and are defined as any polymer material that is biodegradable or bioabsorbable in the body.

As used herein, the term "composite", "composite biodegradable material", "composite biodegradable polymer", "composite bioabsorbable material", "composite bioabsorbable polymer", "composite biomaterial", "composite biodegradable and/or bioabsorbable material" or "composite biodegradable and/or bioabsorbable polymer" are used interchangeably and are defined as two or more polymer materials that are used in combination and are biodegradable or bioabsorbable in the body.

As used herein, the terms "agent", "therapeutic agent", "active agent", "drug", "active drug", and "pharmaceutical agent" are used interchangeably herein and define an agent, drug, compound, composition of matter or mixture thereof which provides some therapeutic, often beneficial, effect. This includes pesticides, herbicides, germicides, biocides, algicides, rodenticides, Fungicides, insecticides, antioxidants, plant growth promoters, plant growth inhibitors, preservatives, antipreservatives, disinfectants, sterilization agents, catalysts, chemical reactants, fermentation agents, foods, food supplements, nutrients, cosmetics, drugs, vitamins, sex sterilants, fertility inhibitors, fertility promoters, microorganism attenuators and other agents that benefit the environment of use. As used herein, the terms further include any physiologically or pharmacologically active substance that produces a localized or systemic effect or effects in animals, including warm blooded mammals, humans and primates; avians; domestic household or farm animals such as cats, dogs, sheep, goats, cattle, horses and pigs; laboratory animals such as mice, rats and guinea pigs; fish; reptiles; zoo and wild animals; and the like. The active drug that can be delivered includes inorganic and organic compounds, including, without limitation, drugs which act on the peripheral nerves, adrenergic receptors, cholinergic receptors, the skeletal muscles, the cardiovascular system, smooth muscles, the blood circulatory system, synoptic sites, neuroeffector junctional sites, endocrine and hormone systems, the immunological system, the reproductive system, the skeletal system, autacoid systems, the alimentary and excretory systems, the histamine system and the central nervous system. Suitable agents may be selected from, for example, proteins, enzymes, hormones, polynucleotides, nucleoproteins, polysaccharides, glycoproteins, lipoproteins, polypeptides, steroids, hypnotics and sedatives, psychic energizers, tranquilizers, anticonvulsants, muscle relaxants, antiparkinson agents, analgesics, anti-inflammatories, local anesthetics, muscle contractants, blood pressure medications and cholesterol lowering agents including statins, antimicrobials, antimalarials, hormonal agents including contraceptives, sympathomimetics, polypeptides and proteins capable of eliciting physiological effects, diuretics, lipid regulating agents, antiandrogenic agents, antiparasitics, neoplastics, antineoplastics, hypoglycemics, nutritional agents and supplements, growth supplements, fats, ophthalmics, antienteritis agents, electrolytes and diagnostic agents.

Examples of the therapeutic agents or drugs 99 useful in this invention include prochlorperazine edisylate, ferrous sulfate, aminocaproic acid, mecaxylamine hydrochloride, procainamide hydrochloride, amphetamine sulfate, methamphetamine hydrochloride, benzphetamine hydrochloride, isoproteronol sulfate, phenmetrazine hydrochloride, bethanechol chloride, methacholine chloride, pilocarpine hydrochloride, atropine sulfate, scopolamine bromide, isopropamide iodide, tridihexethyl chloride, phenformin hydrochloride, methylphenidate hydrochloride, theophylline cholinate, cephalexin hydrochloride, diphenidol, meclizine hydrochloride, prochlorperazine maleate, phenoxybenzamine, thiethylperazine maleate, anisindione, diphenadione, erythrityl tetranitrate, digoxin, iso fluorophate, acetazolamide, methazolamide, bendroflumethiazide, chlorpropamide, tolazamide, chlormadinone acetate, phenaglycodol, allopurinol, aluminum aspirin, methotrexate, acetyl sulfisoxazole, hydrocortisone, hydrocorticosterone acetate, cortisone acetate, dexamethasone and its derivatives such as betamethasone, triamcinolone, methyltestosterone, 17-.beta.-estradiol, ethinyl estradiol, ethinyl estradiol 3-methyl ether, prednisolone, 17-.beta.-hydroxyprogesterone acetate, 19-nor-progesterone, norgestrel, norethindrone, norethisterone, norethiederone, progesterone, norgesterone, norethynodrel, indomethacin, naproxen, fenoprofen, sulindac, indoprofen, nitroglycerin, isosorbide dinitrate, propranolol, timolol, atenolol, alprenolol, cimetidine, clonidine, imipramine, levodopa, chlorpromazine, methyldopa, dihydroxyphenylalanine, theophylline, calcium gluconate, ketoprofen, ibuprofen, atorvastatin, simvastatin, pravastatin, fluvastatin, lovastatin, cephalexin, erythromycin, haloperidol, zomepirac, ferrous lactate, vincamine, phenoxybenzamine, diltiazem, milrinone, captropril, mandol, quanbenz, hydrochlorothiazide, ranitidine, flurbiprofen, fenbufen, fluprofen, tolmetin, alclofenac, mefenamic, flufenamic, difuninal nimodipine, nitrendipine, nisoldipine, nicardipine, felodipine, lidoflazine, tiapamil, gallopamil, amlodipine, mioflazine, lisinopril, enalapril, captopril, ramipril, enalaprilat, famotidine, nizatidine, sucralfate, etintidine, tetratolol, minoxidil, chlordiazepoxide, diazepam, amitriptylin, and imipramine. Further examples are proteins and peptides which include, but are not limited to, insulin, colchicine, glucagon, thyroid stimulating hormone, parathyroid and pituitary hormones, calcitonin, renin, prolactin, corticotrophin, thyrotropic hormone, follicle stimulating hormone, chorionic gonadotropin, gonadotropin releasing hormone, bovine somatotropin, porcine somatropin, oxytocin, vasopressin, prolactin, somatostatin, lypressin, pancreozymin, luteinizing hormone, LHRH, interferons, interleukins, growth hormones such as human growth hormone, bovine growth hormone and porcine growth hormone, fertility inhibitors such as the prostaglandins, fertility promoters, growth factors, and human pancreas hormone releasing factor.

Moreover, drugs or pharmaceutical agents 99 useful for the medical device 50 include: antiproliferative/antimitotic agents including natural products such as vinca alkaloids (i.e. vinblastine, vincristine, and vinorelbine), paclitaxel, epidipodophyllotoxins (i.e. etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagine); antiplatelet agents such as G(GP)I-$I_bIII_a$ inhibitors and vitronectin receptor antagonists; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates—busulfan, nirtosoureas (carmustine (BCNU) and analogs, streptozocin), trazenes—dacarbazinine (DTIC); antiproliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine {cladribine}); platinum coordination complexes (cisplatin, carboplatin), procarbazine, hydroxyurea, mitotane, aminoglutethimide; hormones (i.e. estrogen); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory; antisecretory (breveldin); antiinflammatory: such as adrenocortical steroids (cortisol, cortisone, fludrocortisone, prednisone, prednisolone, 6α-methyl prednisolone, triamcinolone, betamethasone, and dexamethasone), non-steroidal agents (salicylic acid derivatives i.e. aspirin; para-aminophenol derivatives i.e. heteroaryl acetic acids (tolmetin, diclofenac, and ketorolac), arylpropionic acids (ibuprofen and derivatives), anthranilic acids (mefenamic acid, and mectofenamic acid), enolic acids (piroxicam, tenoxicam, phenylbutazone, and oxyphenthatrazone), nabumetone, gold compounds (auranofin, aurothioglucose, gold sodium thiomalate); immunosuppressives: (cyclosporine, tacrolimus (FK-506), sirolimus analogs (rapamycin), azathioprine, mycophenolate mofetil); angiogenic agents: vascular endothelial growth factor (VEGF), fibroblast growth factor (FGF) platelet derived growth factor (PDGF), erythropoetin; angiotensin receptor blocker; nitric oxide donors; anti-sense oligionucleotides and combinations thereof; cell cycle inhibitors, mTOR inhibitors, growth factor signal transduction kinase inhibitors, chemical compound, biological molecule, nucleic acids such as DNA and RNA, amino acids, peptide, protein or combinations thereof.

It is to be understood that the use of the term "agent", "therapeutic agent", "active agent", "drug", "active drug", and "pharmaceutical agent" includes all derivatives, analogs and salts thereof and in no way excludes the use of two or more such agents, therapeutic agents, active agents, drugs, active drugs, or pharmaceutical agents.

The present invention as best illustrated in FIGS. 1-9 is a medical device 50 such as a medical implant constructed of biodegradable and/or bioabsorbable polymers that are either natural or synthetic. In general, synthetic polymers offer greater advantages than natural materials in that they can be tailored to give a wider range of properties and more predictable lot-to-lot uniformity than can materials from natural sources. Synthetic polymers also represent a more reliable source of raw materials, one free from concerns of immunogenicity.

The general criteria for selecting a polymer for use as a biomaterial (a biodegradable and/or bioabsorbable material) is to match the mechanical properties and the time of degradation to the needs of the application. The ideal polymer for a particular application is configured so that it: (i) has mechanical properties that match the application, remaining sufficiently strong until the surrounding tissue has healed, (ii) does not invoke an inflammatory or toxic response, (iii) is metabolized in the body after fulfilling its purpose, leaving no trace, (iv) is easily processable into the final product form, (v) demonstrates acceptable shelf life, and (vi) is easily sterilized.

The factors affecting the mechanical performance of biodegradable polymers are those that are well known to the polymer scientist, and include monomer selection, initiator selection, process conditions, and the presence of additives. These factors in turn influence the polymer's hydrophilicity, crystallinity, melt and glass-transition temperatures, molecular weight, molecular-weight distribution, end groups, sequence distribution (random versus blocky), and presence of residual monomer or additives.

In addition, the polymer scientist working with biodegradable materials must evaluate each of these variables for its effect on biodegradation. Biodegradation has been accomplished by synthesizing polymers that have hydrolytically unstable linkages in the backbone. The most common chemical functional groups with this characteristic are esters, anhydrides, orthoesters, and amides.

Preferably, the medical device 50 has a structure, components or features at least one biodegradable and/or bioabsorbable polymer that has crystalline, semi-crystalline and amorphous characteristics. The degradation mechanism of semi-crystalline bioabsorbable polymers is mainly by hydrolysis of ester linkages or other labile bonds or hydrolytically unstable backbone. This is the most prevailing mechanism for polymer degradation. In general, the degradation occurs in two phases. In the first phase, hydrolysis of amorphous phase occurs and forms low molecular weight water-soluble fragments e.g., lactic acid. This reduction in molecular weight in the amorphous phase does not result in reduction in mechanical properties as the crystalline regions provide the required strength to the structure. Then, hydrolysis of crystalline phase occurs which results in loss in molecular weight and mechanical properties. This is followed by enzymatic attack that leads to metabolism of fragments and results in accelerated polymer mass loss. These fragments then enter the Kreb's Cycle and are excreted as carbon dioxide and water. This degradation process can vary from days to months to years and it depends on the type of polymer. The factors that accelerate polymer degradation includes hydrophilic backbone and end groups, less crystallinity, more porosity and higher surface area, no orientation, no physical aging, low density, presence of additives such as plasticizers and water soluble or leachable materials.

Additionally, it is well established that the degradation of polymers, such as polylactic acid (PLA) and polyglycolic acid (PGA) are catalyzed by carboxyl end groups formed by chain cleavage and that amorphous regions are preferentially degraded. See Suming Li, "Hydrolitic Degradation Charcteristics of Aliphatic Polyesters Derived from Lactic and Glycolic Acids", *J Biomed Mater Res (Appl Biomatter)* 48: 342-353 (1999). In general, the cleavage of an ester bond yields a carboxyl end group and a hydroxyl end group wherein the formed carboxyl end groups are capable of catalyzing hydrolysis of other ester bonds. This process is commonly known as autocatalysis.

One example of fast degradation of PLA polymers is the degradation of PLA in a phosphate buffer wherein in about a 5-week period of degradation, the PLA material becomes heterogeneous with the interior of the material being composed of various viscous oligomers. This degradation process is known as "heterogeneous degradation" or "faster internal degradation".

Thus, in an aqueous medium, water penetrates into the polymer material which results in the hydrolytic cleavage of the ester bonds wherein the cleavage of the ester bonds forms a new carboxyl end group thereby accelerating the reaction of the other ester bonds through autocatalysis. As part of this process, initially, the degradation occurs in bulk and is macroscopically homogeneous. However, when soluble oligomers are generated, those oligomers near the surface of the matrix escape from the matrix before being completely degraded whereas those oligomers trapped within the matrix results in a higher acidity within the polymer matrix than at the surface of the matrix. Thus, the autocatalysis is greater in the bulk (within the matrix) than at the surface of the matrix and as the degradation of the polymer continues more carboxyl end groups are formed inside the matrix leading to an accelerated internal degradation. Eventually, hollow structures are formed in the material by this degradation phenomenon.

The above-outlined degradation process has been identified for those polymers containing PLA and PGA, for example, $PLA_{75}GA_{25}$; $PLA_{85}GA_{15}$; $PLA_{87.5}$; $PLA_{96}$; and $PLA_{100}$.

Bioabsorbable and/or biodegradable polymers consist of bulk and surface erodable materials. Surface erosion polymers are typically hydrophobic with water labile linkages. Hydrolysis tends to occur fast on the surface of such surface erosion polymers with no water penetration in bulk. The initial strength of such surface erosion polymers tends to be low however, and often such surface erosion polymers are not readily available commercially. Nevertheless, examples of surface erosion polymers include polyanhydrides such as poly(carboxyphenoxy hexane-sebacic acid), poly(fumaric acid-sebacic acid), poly(carboxyphenoxy hexane-sebacic acid), poly(imide-sebacic acid) (50-50), poly(imide-carboxyphenoxy hexane) (33-67), and polyorthoesters (diketene acetal based polymers).

Bulk erosion polymers, on the other hand, are typically hydrophilic with water labile linkages. Hydrolysis of bulk erosion polymers tends to occur at more uniform rates across the polymer matrix of the device. Bulk erosion polymers exhibit superior initial strength and are readily available commercially.

Examples of bulk erosion polymers include poly($\alpha$-hydroxy esters) such as poly(lactic acid), poly(glycolic acid), poly(caprolactone), poly(p-dioxanone), poly(trimethylene carbonate), poly(oxaesters), poly(oxaamides), and their copolymers and blends. Some commercially readily available bulk erosion polymers and their commonly associated medical applications include poly(dioxanone) [PDS® suture available from Ethicon, Inc., Somerville, N.J.], poly(glycolide) [Dexon® sutures available from United States Surgical Corporation, North Haven, Conn.], poly(lactide)-PLLA [bone repair], poly(lactide/glycolide) [Vicryl® (10/90) and Panacryl® (95/5) sutures available from Ethicon, Inc., Somerville, N.J.], poly(glycolide/caprolactone (75/25) [Monocryl® sutures available from Ethicon, Inc., Somerville, N.J.], and poly(glycolide/trimethylene carbonate) [Maxon® sutures available from United States Surgical Corporation, North Haven, Conn.].

Other bulk erosion polymers are tyrosine derived poly amino acid [examples: poly(DTH carbonates), poly(arylates), and poly(imino-carbonates)], phosphorous containing polymers [examples: poly(phosphoesters) and poly(phosphazenes)], poly(ethylene glycol) [PEG] based block co-polymers [PEG-PLA, PEG-poly(propylene glycol), PEG-poly(butylene terephthalate)], poly($\alpha$-malic acid), poly(ester amide), and polyalkanoates [examples: poly(hydroxybutyrate (HB) and poly(hydroxyvalerate) (HV) co-polymers].

Of course, the devices may be made from combinations of surface and bulk erosion polymers in order to achieve desired physical properties and to control the degradation mechanism. For example, two or more polymers may be blended in order to achieve desired physical properties and device degradation rate. Alternately, the device may be made from a bulk erosion polymer that is coated with a surface erosion polymer. The drug delivery device may be made from a bulk erosion polymer that is coated with a drug containing a surface erosion polymer. For example, the drug coating may be sufficiently thick that high drug loads may be achieved, and the bulk erosion polymer may be made sufficiently thick that the mechanical properties of the device are maintained even after all of the drug has been delivered and the surface eroded. Alternately, the device can also be formed from layers of different polymer and drug combinations to provide programmable drug release during polymer absorption. Accordingly, in these embodiments according to the present invention, the drug 99 (which may include only one or combinations of different drugs, i.e. more than one type of drug 99) is programmably released from one or both of the first biodegradable and/or bioabsorbable material 75 and the second biodegradable and/or bioabsorbable material 80 as different polymer layers.

Referring now to FIG. 1, the present invention is a biodegradable and/or bioabsorbable medical device, generally designated 50, for placement or implantation in a patient's body. The medical device 50 is any type of medical device, such as a medical implant, and in this example, the medical device 50 is a stent for deployment within a vessel. The medical device 50 has a composite structure of a first biodegradable and/or bioabsorbable material 75 that degrades at a first degradation rate and a second biodegradable and/or bioabsorbable material 80 layered or coated over or blended with the first biodegradable and/or bioabsorbable material 75, wherein the first degradation rate of the first biodegradable and/or bioabsorbable material 75 is faster than the second degradation rate of the second biodegradable and/or bioabsorbable material 80 in accordance with the present invention.

Particularly, the medical device 50 is made of composite structures comprising different biodegradable and/or bioabsorbable material 75 and 80 respectively including coatings or layers or blends of different biodegradable and/or bioabsorbable material 75 and 80 respectively. Each of the biodegradable and/or bioabsorbable materials 75 and 80 respectively has a different degradation rate. And, the medical device 50 is designed such that the second biodegradable and/or bioabsorbable material 80 has a degradation rate that is slower than the degradation rate of the first biodegradable and/or bioabsorbable material 75. And, as will be described in greater detail later in this disclosure, the second biodegradable and/or bioabsorbable material 80 is coated or layered over the first biodegradable and/or bioabsorbable material 75 and both first biodegradable and/or bioabsorbable material 75 and second biodegradable and/or bioabsorbable material 80 are selected and configured or arranged in such a way such that a desired mass loss is achieved to include an accelerated degradation after the medical device has achieved its desired functional effect or achieved the end of its functional purpose or useful life. This period of accelerated degradation occurs after the second biodegradable and/or bioabsorbable material 80 coating or layer(s) has degraded thereby exposing portions of the first biodegradable and/or bioabsorbable material 75. Thus, the period of accelerated degradation occurs at a point in time after the medical device 50 has achieved its functional purpose or useful life.

In one embodiment according to the present invention, medical device 50 (FIGS. 1-5) is made from composite structures wherein the first structure (first biodegradable and/or bioabsorbable material 75) serves as a polymer core or polymer backbone and has physical properties and characteristics that enable rapid degradation through hydrolysis upon exposure. The second biodegradable and/or bioabsorbable material 80 coating or layer(s) over the first structure 75 has physical properties and characteristics resulting in a slower degradation rate than the degradation rate of the first structure 75. One example is to use poly-L-(lactic acid) (PLLA) on the surface (e.g., as a thick layer or coating) to serve as the second biodegradable and/or bioabsorbable material 80 of the device 50 and poly(glycolic acid) (PGA) as the first biodegradable and/or bioabsorbable material 75 to serve as the core or backbone of the device 50. Both of these materials 75 and 80 provide stiffness to the device 50 (in this example, thereby allowing the stent 50 to keep a vessel propped open) until the functional effect of the device 50 is achieved or the device 50 has reached the end of its functional purpose or useful life. Accordingly, device 50 is designed such that as the functional end of the device 50 is being achieved the PLLA material 80 degrades and exposes the PGA material core 75 that, in turn, degrades very rapidly, i.e. at a much greater degradation rate than the PLLA material coating 80. The absorption of PGA will make the device porous and will increase the surface area and will accelerate the rate of absorption of any remaining PLLA. This permits the entire device 50 to be completely eliminated from the patient's system after the device 50 has concluded its functional purpose or useful life. Other derivatives of PLLA and PGA can be used in addition to other polymers to achieve the desired absorption profile. Examples of other materials for 80 include DLPLA; PLA/PGA copolymers (95/5; 85/15); PLA-PCL copolymers that have lower absorption time than PLLA. Accordingly, appropriate examples for the second biodegradable and/or bioabsorbable material 80 include polylactide based polymers, polyglycolide based polymers, poly($\alpha$-hydroxy esters) such as poly (lactic acid), poly(glycolic acid), poly(caprolactone), poly(p-dioxanone), poly(trimethylene carbonate), poly(oxaesters), poly(oxaamides, poly(lactide)-PLLA, poly(lactide/glycolide), poly(glycolide/caprolactone) (75/25), poly(glycolide/trimethylene carbonate), tyrosine derived poly amino acid, poly(DTH carbonates), poly(arylates), poly(imino-carbonates), phosphorous containing polymers, poly(phosphoesters) and poly(phosphazenes), poly(ethylene glycol) based block co-polymers, PEG-PLA, PEG-poly(propylene glycol), PEG-poly(butylene terephthalate), poly($\alpha$-malic acid), poly (ester amide), polyalkanoates, poly(hydroxybutyrate (HB), poly(hydroxyvalerate) (HV) co-polymers, DLPLA; PLA/PGA copolymers (95/5; 85/15); PLA-PCL copolymers that have lower absorption time than PLLA and their co-polymers and blends.

Examples of other materials for 75 include PGA/PLA (90/10); PGA/PCL (75/25; 50/50; 65/35); poly(p-dioxanone) and their derivatives that have longer absorption time than PGA.

Other examples for 75 include poly(ethylene glycol); citrate esters and other water soluble materials that will dissolve and create a higher surface area for faster absorption of 80. Accordingly, appropriate examples for the first biodegradable and/or bioabsorbable material 75 include poly(glycolic acid) (PGA), poly(α-hydroxy esters), polyanhydrides such as poly (carboxyphenoxy hexane-sebacic acid), poly(fumaric acid-sebacic acid), poly(carboxyphenoxy hexane-sebacic acid), poly(imide-sebacic acid) (50-50), poly(imide-carboxyphenoxy hexane) (33-67), tyrosine derived poly amino acid, polyorthoesters (diketene acetal based polymers), phosphorous containing polymers, poly(ethylene glycol); citrate esters and other water soluble materials that will dissolve and create a higher surface area for faster absorption and their co-polymers and blends.

Although medical device 50 is not limited to any particular configuration, in certain embodiments according to the present invention, medical device 50 has a substantially cylindrical configuration and is substantially hollow along its longitudinal axis and terminates at an open end at each end of its cylindrical configuration. Accordingly, the configuration of medical device 50 in accordance with the present invention and as described above is best suited as a stent for placement within a vessel for treatment of cardiovascular disease such as stenosis, artherosclerosis, vulnerable plaque, or ischemic heart disease or as a valve such as a heart valve for regulating blood flow.

Medical device 50 has structure, features and components 70 that optionally include hoops, loops, flexible links or bridges or extensions (not shown) that are either made of a first biodegradable and/or bioabsorbable material 75 which can be in the form of one or more layers or coatings or blends. Additionally, first biodegradable and/or bioabsorbable material 75 is the core which is coated with second biodegradable and/or bioabsorbable material 80, i.e. second material 80 serves as an initial protective coating for the first biodegradable and/or bioabsorbable material 80 (based on the dramatic differences in the degradation rates of the materials 75 and 80 respectively).

The first biodegradable and/or bioabsorbable material 75 is used as the base material for structural aspects 70 of the device 50 such as hoops, loops, flexible links or bridges or extensions of the stent 50 or the housing, flaps or other components 70 of the desired medical device 50. When applied as a coating 80, the second biodegradable and/or bioabsorbable material 80 is used as the coating material 80 to be coated over and initially protect the structural aspects 75 of the device or stent 50 such as hoops, loops, flexible links or bridges or extensions of the stent 50 or the other components of the desired medical device 50.

By way of example, the first biodegradable and/or bioabsorbable material 75 is a bulk erodible polymer (either a homopolymer, copolymer or blend of polymers) such as any one of the polyesters belonging to the poly(alpha-hydroxy acids) group. This includes aliphatic polyesters such poly (lactic acid); poly(glycolic acid); poly(caprolactone); poly(p-dioxanone) and poly(trimethylene carbonate); and their copolymers and blends. Other polymers useful as the first bioabsorbable material 75 include amino acid derived polymers [e.g., poly(iminocarbonates)]; phosphorous containing polymers [e.g., poly(phosphazenes); poly(phosphoesters)] and poly(ester amide).

The rate of hydrolysis of the first biodegradable and/or bioabsorbable material 75 depends on the type of monomer used to prepare the bulk erodible polymer. For example, the absorption times (time to complete degradation or fully degrade) are estimated as follows: poly(caprolactone), poly (trimethylene carbonate) and poly(1-lactic acid) takes about 2-4 years; poly(dioxanone) takes about 7 months; and poly (glycolic acid) takes about 3-6 months. Preferably, the degradation rate for the first biodegradable and/or bioabsorbable material 75 is between 1 day and 3 months.

Absorption rates for copolymers prepared from the monomers such as poly(lactic acid-co-glycolic acid); poly(glycolic acid-co-caprolactone); and poly(glycolic acid-co-trimethylene carbonate) depend on the molar amounts of the monomers. The degradation of the polymers is by hydrolysis and the byproducts are typically water soluble fragments such as monomers that are used to prepare the polymers [for example, lactic acid from poly(lactic acid); glycolic acid from poly (glycolic acid)] which are metabolized by enzymatic attack then enters the kreb's cycle and excreted as carbon dioxide and water.

In accordance with the present invention, the second biodegradable and/or bioabsorbable material 80 is having a much slower rate or hydrolysis (degradation rate) than the biodegradable and/or bioabsorbable material 75. For example, based on the hydrolysis rates outlined above, PLLA is one appropriate material for the coating 80 and PGA as an appropriate material for the core 75 of the device 50. For example, preferably, the degradation rate for the second biodegradable and/or bioabsorbable material 80 is between 3 months and 48 months.

Figure 3:
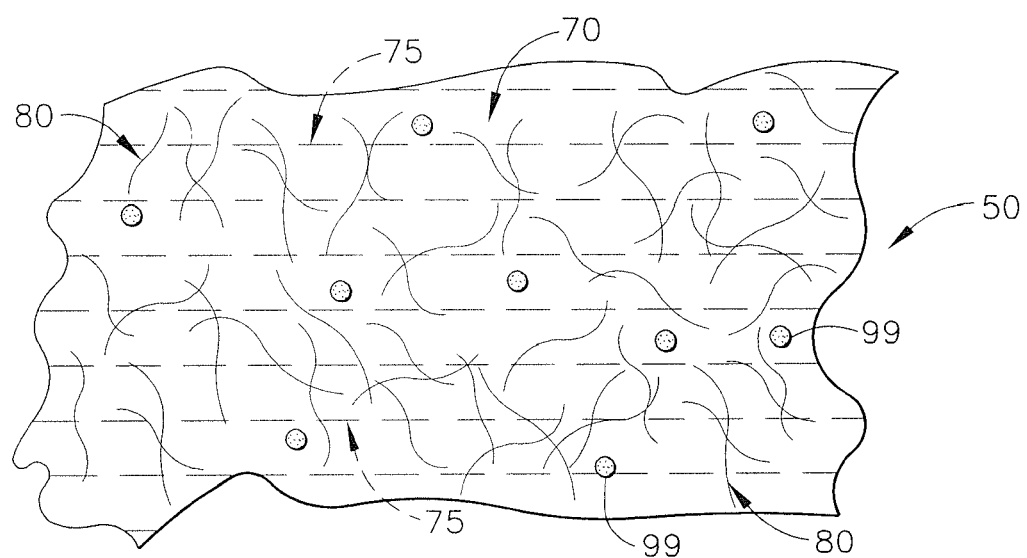
FIG. 3 is a schematic illustration of a portion of structure of the medical device of FIG. 1 wherein a drug is incorporated therein for release in accordance with the present invention.

FIG. 3 illustrates a further embodiment of the medical device 50 depicted in FIG. 1 wherein the device 50 further includes a drug 99 which is incorporated into one or more portions of the device, for example, drug 99 incorporated into the outer coating layer(s) of the second biodegradable and/or bioabsorbable material 80 or within the polymer core or backbone material 75 (first biodegradable and/or bioabsorbable material 75 which is the basis of the structure, components or features of the of the medical device 50) or drug 99 incorporated into both materials 75 and 80 respectively.

Thus, in the example where the medical device 50 is a stent, the device 50 depicted in FIG. 3, is a drug-eluting stent wherein drug 99 is released from the stent 50 according to a pre-determined drug release profile. Moreover, the degradation or hydrolysis rates of the outer material 80 and the inner core 75 are timed to coincide with the desired drug release profile. Details of an exemplary drug 99 used with the stent 50 as a drug delivery system based on degradation parameters according to a desired or pre-determined mass loss curve for the stent 50 itself including an accelerated degradation phase after achieving the desired drug release profile, i.e. after the stent 50 has achieved its functional purpose of delivering its drug 99 into the vessel wall in which it is implanted will be described in greater detail later in this disclosure. Additionally, one or more drugs 99 can be used in the medical device 50 in accordance with the present invention.

Figure 4:
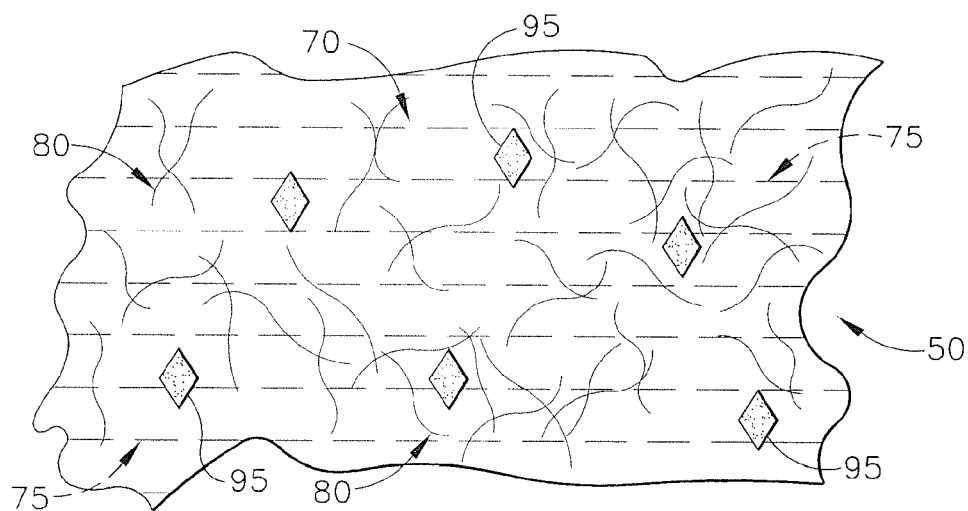
FIG. 4 is a schematic illustration of a portion of structure of the medical device of FIG. 1 wherein an additive such as a degradation additive, buffering agent, radiopaque agent or the like is incorporated therein for release in accordance with the present invention.

FIG. 4 is a further embodiment of the medical device 50 of FIG. 1 wherein the device 50 includes an additive 95 such as a degradation additive, buffering agent, radiopaque agent or the like for release upon degradation of the material 80 and/or material 75 in accordance with the present invention. Additionally, one or more additives 95 can be used in the medical device 50 in accordance with the present invention. Highly reactive enzymes, for example such as Proteinase K, are particularly useful as degradation additives 95 for use with the medical device 50 according to the present invention.

Figure 5:
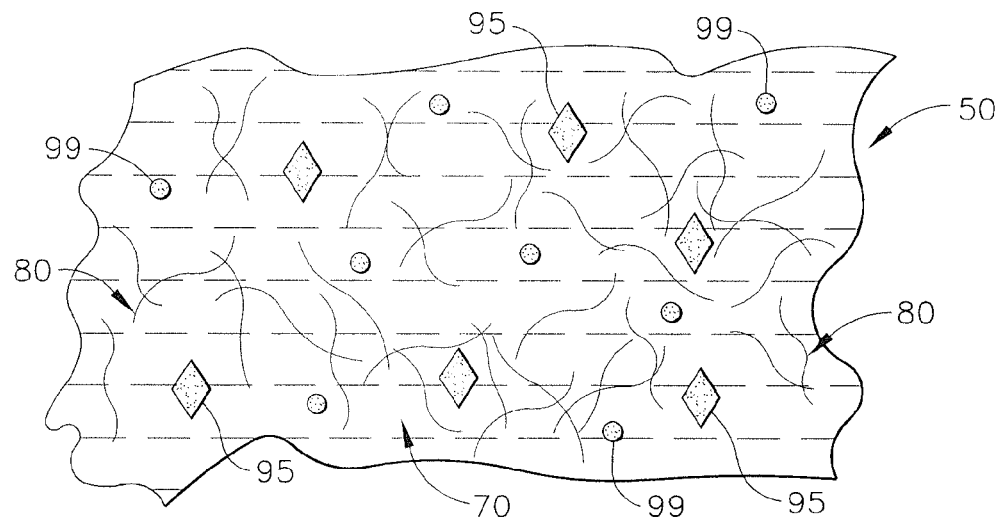
FIG. 5 is a schematic illustration of a portion of structure of the medical device of FIG. 1 wherein both an additive such as a degradation additive, buffering agent, radiopaque agent or the like and a drug are incorporated therein for release in accordance with the present invention.

FIG. 5 is a further embodiment of the medical device 50 of FIG. 1 wherein the device 50 includes both drug 99 and an additive 95 such as a degradation additive, buffering agent, radiopaque agent or the like for release upon degradation of the material 80 and/or material 75 in accordance with the present invention. Additionally, one or more drugs 99 can be used in combination with one of more additives 95 in the medical device 50 in accordance with the present invention.

Figure 6:
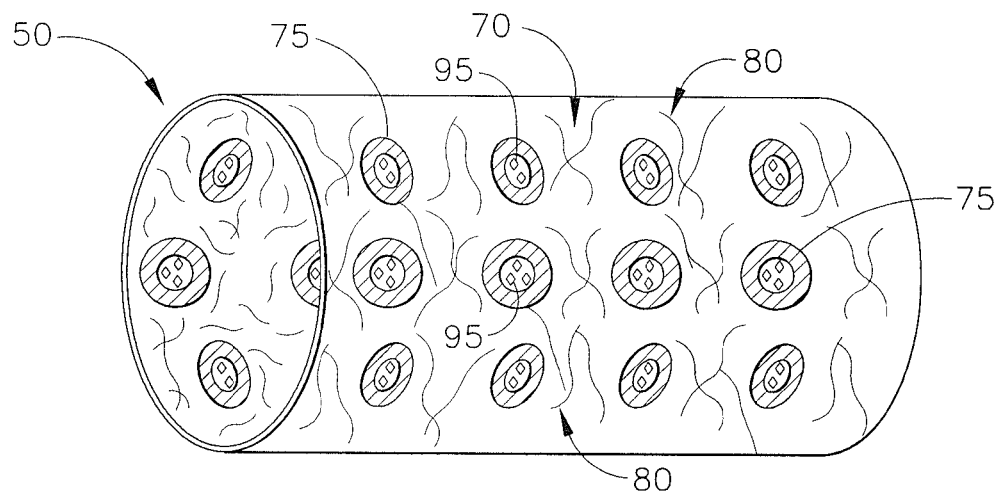
FIG. 6 is a schematic illustration of a medical device having a composite structure of a first biodegradable and/or bioabsorbable material and an encapsulated degradation additive, shown as a cross-sectional slice taken from a sphere, in accordance with the present invention.
Figure 7:
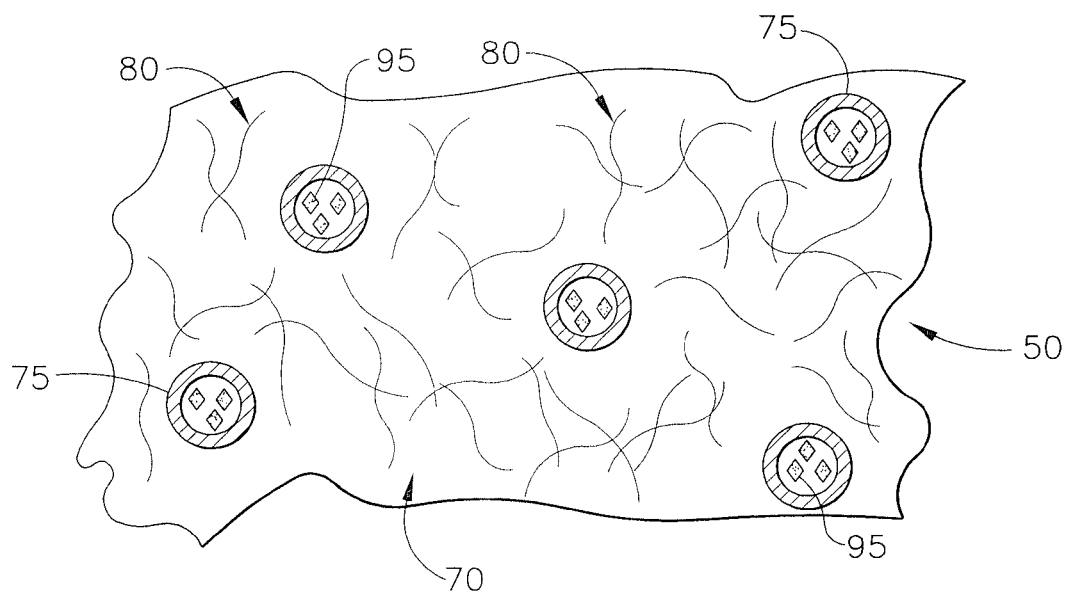
FIG. 7 is a schematic illustration of a portion of structure of the medical device of FIG. 6 in accordance with the present invention.

Additionally, as best illustrated in FIG. 6 and FIG. 7, the present invention is also directed to a new and useful medical device 50 that is made of biodegradable and/or bioabsorbable material 80 which can be either the main structure 70 of the device 50 and can also be in the form of one or more coatings or blends or layers of the biodegradable and/or bioabsorbable material 80. PLLA is one example polymer that has been identified to be particularly useful as the biodegradable and/or bioabsorbable material 80 for the main structure 70. Additionally, device 50 further includes encapsulated degradation additives 95 encapsulated in the biodegradable and/or bioabsorbable material 75 that upon release (upon hydrolysis of the encapsulating material 75) will preferentially cleave the polymer backbone material 80. PGA is one example polymer that has been identified to be particularly useful as the biodegradable and/or bioabsorbable material 75 for the main structure 70. Examples of the degradation additives 95 are selected enzymes, high pH materials, etc. One particularly useful enzyme as degradation additive 95 is proteinase K encapsulated in PGA.

There are several enzymes that can be used for the degradation of bioabsorbable materials. Enzymatic degradation of polymers depends on the specificity of enzymes. In vitro degradation studies using enzymes are generally conducted at 37° C. at pH of about 6 to 8.6 in buffer (phosphate or Tris/HCl) in the presence of sodium azide. Proteinase-K, Bromelain and Pronase were amongst the first enzymes that were used to demonstrate enzymatic degradation of PLLA. The enzyme hydrolyses amide and ester bonds. Proteinase-K is very effective and has been used to study degradation of PLLA and copolymers. It is a serine protease produced by *Trilirachium album*, a fungus that grows on native keratin as its sole carbohydrate and nitrogen source. It has been observed that this enzyme will preferentially degrade L-lactyl units as opposed to D-lactyl ones, and poly(D-lactide) is not degradable. The enzyme degrades L-L, L-D and D-L bonds as opposed to D-D bond. The degradation preferentially occurs in the amorphous regions of semi-crystalline PLLA. It cannot degrade the crystalline domains of PLLA and PCL. This is due to the fact that the active site of Proteinase-K preferentially hydrolyses at the disordered chain-packing regions of crystal edges rather than the chain-folding surfaces of single crystals. Water uptake will lead to swelling of the polymer and will facilitate enzymatic attack.

Enzymatic degradation of PCL has been investigated in the presence of lipase-type enzymes. These enzymes are capable of cleaving ester bonds on hydrophobic surface. Three types of lipase significantly accelerate the degradation of PCL namely, *R. delemer* lipase, *Rhizopus arrhizus* lipase and *Pseudomonase* lipase. Highly crystalline PCL is totally degraded in 4 days, therefore these enzymes can degrade amorphous and crystalline phases of the polymer. These enzymes cannot degrade PLLA.

An *Amycolatopsis* sp. strain HT-32 has been successfully isolated and used to demonstrate degradation of PLLA. Further isolation of PLLA degrading microorganisms has led to the isolation of four actinomycetes and four bacteria. One actinomycetes has been identified as *Amycolatopsis* sp. (strain 41) on the basis of morphological observations and analysis of 16s RNA. Isolation of PLLA degrading actinomycete is taxonomically similar to the *Amycolatopsis* strain. *Amycolatopsis* strain is able to degrade PLLA. 25 reference strains belonging to genus *Amycolatopsis*, 15 are able to form clear zones on an agar plate emulsified with PLLA. Therefore, *Amycolatopsis* plays an important role in the biodegradation of PLLA. Enzyme can be produced from *Amycolatopsis* sp (strain 41) with an estimated molecular weight of about 40 to 42 KDa with an optimum pH and temperature of 6.0 and 37-45° C., respectively, for highest activity. This enzyme will preferentially degrade PLLA but not poly(ε-caprolactone) and poly(β-hydrobutyrate).

Poly(hydroxybutyrate) [PHB] and its copolymers can be enzymatically degraded by extracellular PHB depolymerases isolated from various environments such as *Pseudomonas lemoignei, Alcaligenes faecalis, Comamonas testosteroni, Pseudomonas stutzeri, Pseudomonas pickettii* and *Comamonas acidovorans*. These enzymes attack preferentially at the disordered chain packing regions of the crystal edge rather than the chain folding surfaces of the crystalline structure.

Therefore, selection of the enzyme or degradation additive is based on the type of material that needs to degraded in a short time.

Since the degradation rate of polymer material 75 is greater than the degradation rate of the polymer core material 80, as soon as the encapsulation material 75 is sufficiently degraded, the degradation additive 95 is released and acts upon the polymer core material 80 thereby increasing the degradation rate of polymer core material 80 in order to achieve a desired mass loss for the device 50.

Again, for this embodiment as well, additive 95 can be either a degradation additive, buffering agent, radiopaque agent or the like for release upon degradation of the encapsulation material 75 in accordance with the present invention. Additionally, one or more additives 95 can be used in the medical device 50 in accordance with the present invention. Highly reactive enzymes, for example such as Proteinase K, are particularly useful as degradation additives 95 for use with the medical device 50 according to the present invention.

Figure 8:
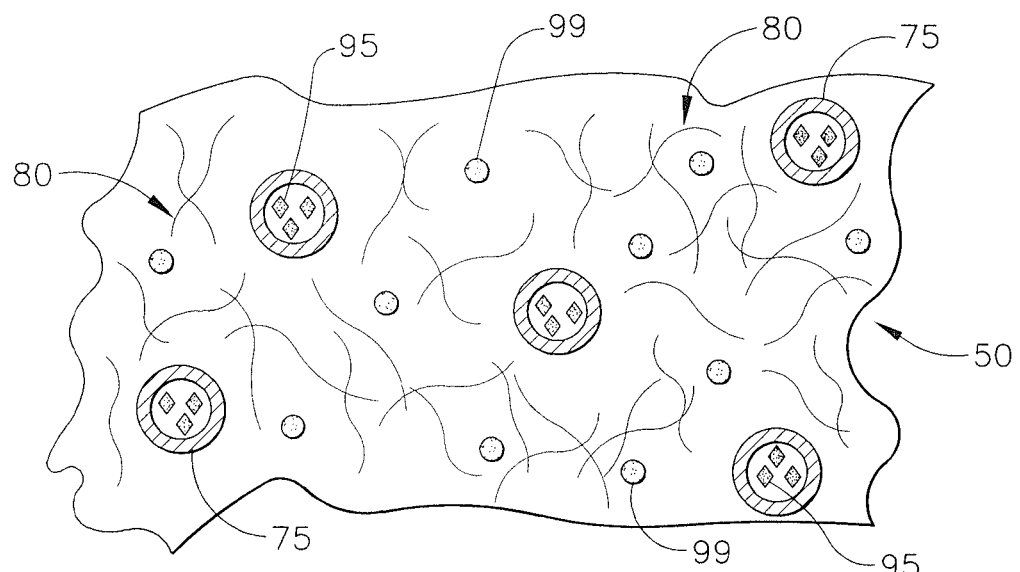
FIG. 8 is a schematic illustration of a portion of structure of the medical device of FIG. 6 wherein a drug is incorporated therein for release in accordance with the present invention.
Figure 9:
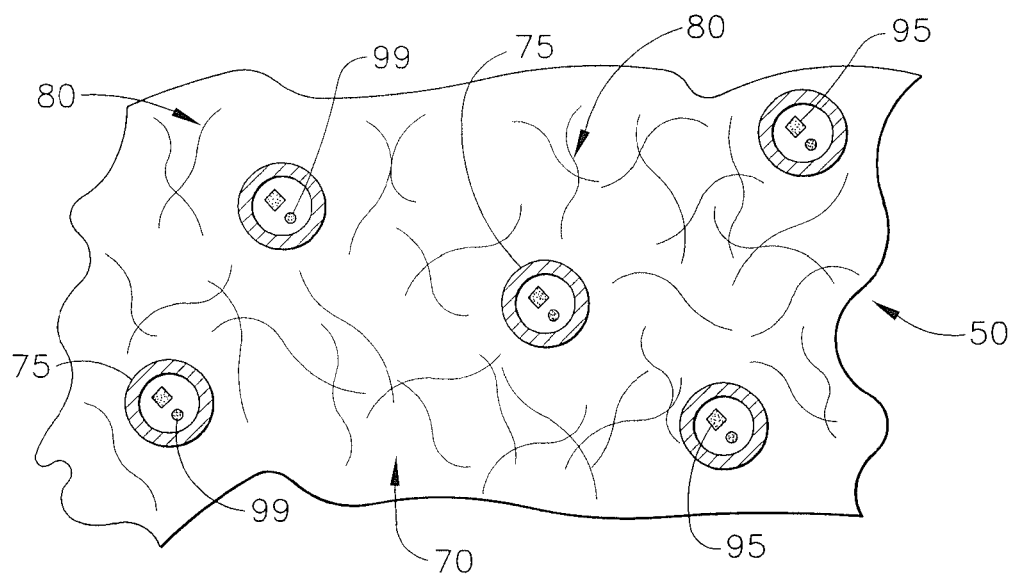
FIG. 9 is a schematic illustration of a portion of structure of the medical device of FIG. 6 wherein both a degradation additive and a drug are encapsulated therein, shown as a cross-sectional slice taken from a sphere, for release in accordance with the present invention.

Moreover, as shown in FIGS. 8 and 9 respectively, drug 99 is incorporated into one or more portions of the device 50, for example, drug 99 incorporated directly into the biodegradable and/or bioabsorbable material 80 (which is the basis of the structure, components or features of the of the medical device 50 as shown in FIG. 8) or encapsulated together with degradation additive 95 within the biodegradable and/or bioabsorbable material 75 as shown in FIG. 9. Additionally, drug 99 can be incorporated into both materials 75 and 80 respectively.

Thus, in the example where the medical device 50 is a stent, the device 50 depicted in FIG. 8 and FIG. 9, is a drug-eluting stent wherein drug 99 is released from the stent 50 according to a pre-determined drug release profile. Moreover, the degradation or hydrolysis rates of the encapsulation polymer material 75 and ultimately the main structure polymer material 80 are timed to coincide with the desired drug release profile. Details of an exemplary drug 99 used with the stent 50 as a drug delivery system based on degradation parameters according to a desired or pre-determined mass loss curve for the stent 50 itself including an accelerated degradation phase after achieving the desired drug release profile, i.e. after the stent 50 has achieved its functional purpose of delivering its drug 99 into the vessel wall in which it is implanted will be described in greater detail later in this disclosure. Additionally, one or more drugs 99 can be used in the medical device 50 in accordance with the present invention.

Accordingly, for the medical device embodiments of FIGS. 6-9, the biodegradable and/or bioabsorbable material 80 for the stent structure has a much slower rate of hydrolysis (degradation rate) that the biodegradable and/or bioabsorbable material 75 used as the encapsulation material. For example, based on the hydrolysis rates outlined above, PLLA is an appropriate material for the main structure 80 of the device 50 and PGA is one appropriate material for the encapsulation material 75. Thus, the PGA of the encapsulation material 75 will degrade at a much faster rate thereby releasing the degradation additive 95, for example proteinase K, (as well as one or more drugs 99 and other desired additives 95, such as buffering agents or radiopaque agents, encapsulated therein) which will enzymatically react with the PLLA structure material 80 in order to accelerate hydrolysis of the device 50.

The encapsulation of the degradation additive 95 or other additives (such as buffering agent or radiopaque agent) can be in the form of microparticles or nanoparticles that do not adversely affect the physical properties of the device 50.

Different types of buffering agents 95, such as inorganic basic fillers, can be used with all embodiments of the device 50 in accordance with the present invention. Some examples of these basic compounds for use as buffering agents include calcium hydroxyapatite; carbonated apatite; tricalcium phosphate; calcium carbonate; sodium bicarbonate; calcium phosphates; carbonated calcium phosphates; and magnesium hydroxide. Also, acid/based titrating compounds (amine monomers); and lactate dehydrogenase (it will convert lactate in to pyruvate which is the end product of glycolysis and starting component of Citric acid cycle) can also be used as the buffering agent 95.

The inorganic fillers 95 will react with the acid, and neutralize the acid that is formed during the absorption of the polymers 75 and 80. So, they behave as the buffering agents and prevent the acid content in the immediate environment to be maintained at pH ranging from about 5 to about 7 and more preferably at pH ranging from about 6 to about 7.4. The total amount of inorganic filler or buffering agent 95 should be sufficient to neutralize the total amount of acid that is generated during the absorption process. For example, 1 mole of calcium carbonate is needed to react with 2 mol of lactic acid (see below):

$$CaCO_3(solid) + 2CH_3CH(OH)-COOH(aqueous) \Rightarrow Ca^{2+}(aq) + H_2O + CO_2(aq) + 2CH_3CH(OH)-COO^-(aq)$$

A method of formulating the biomaterial structure, materials or coatings or blends 75 and 80 of the medical device 50 is described in greater detail later below. This method is also applicable for combining with degradation additives 95 (or other additives such as buffering agents or radiopaque agents), and therapeutic agent or drug 99 which can be mixed together with the polymer material of the device 50 in some embodiments or mixed with the biodegradable and/or bioabsorbable material 75 for encapsulating both the degradation additive 95, and optionally together with the drug 99.

Types of appropriate degradation additives 95 include buffers such as bioactive glasses, ceramics and calcium phosphates which are used to stabilize the pH of the environment surrounding the device 50 in order to control the degradation of the biomaterial structure, materials or coatings or blends 75 and 80 of the medical device 50. See K. Rezwan et al. "Biodegradable and Bioactive Porous Polymer/Inorganic Composite Scaffolds for Bone Tissue Engineering", *Biomaterials* 27 (2006) 3413-3431. In general, the basic components of bioactive glasses useful for the medical device 50 in accordance with the present invention are $SiO_2$, $NA_2O$, $CaO$ and $P_2O_5$. One particular type of bioactive glass useful as the degradation additive 95 is 45S5 BIOGLASS® (University of Florida) which is a bioactive glass containing 45% $SiO_2$, 24.5% $NA_2O$, 24.4% $CaO$ and 6% $P_2O_5$ in weight percent.

The use of bioactive glasses as part of the scaffold material of the medical device 50 in order to control degradation of the device 50 is to control a range of chemical properties as well as the rate of bioresorption upon degradation of the device 50. Thus, the structure and chemistry of the bioactive glasses used in the present invention, such as sol-gel derived glasses, can be customized at the molecular level through varying such factors as the composition, thermal properties or environmental processing history.

Additionally, degradation of the medical device 50 in accordance with the present invention is also accomplished through adding bioactive phases to the biodegradable and/or bioabsorbable material 75 and 80. Addition of bioactive phases to polymers used in the material 75 and 80 alter the polymer degradation behavior, by allowing rapid exchange of protons in water for alkali in the glass or ceramic. This mechanism is suggested to provide a pH buffering effect at the polymer surface, thereby modifying the acidic polymer degradation. Inclusion of bioactive glasses into the medical device 50 can modify surface and bulk properties of the device 50 itself, including any composite scaffolds, by increasing the hydrophilicity and water absorption of the hydrophobic polymer matrix, thus altering the degradation kinetics of the device 50. In particular, the inclusion of 45S5 BIOGLASS® particles can increase water absorption compared to pure polymer foams such as PDLLA and PLGA. It is also known that polymer composites filled with hyaluronic acid (HA) particles hydrolyzed homogeneously due to water penetrating the interfacial regions of the scaffold.

As described in Rezwan et al., in vitro studies in phosphate-buffered saline at 37° C. showed that the addition of bioactive glass, such as BIOGLASS®, increased water absorption and weight loss in comparison to pure polymer foams.

Other types of degradation additives 95 are also important for the medical device 50 in accordance with the present invention. For example, either acidic compounds or basic compounds can be incorporated into the polymeric matrix of the device 50. Incorporation of acidic compounds can accelerate the degradation of the polymers used in the device 50. Whereas, incorporation of basic compounds can achieve two effects simultaneously, i.e. base catalysis and neutralization of carboxyl end groups. Whether the degradation of the device 50 is accelerated or slowed down depends on the relative importance of these effects.

For example, a buffer 95 such as the inorganic compound of coral (containing granules of calcium carbonate) was first used in medical implants made of PLA and coral blend matrix in order to slow degradation of the polymer implant in order to facilitate bone tissue regeneration. And, it has been proven that large amounts of coral granules creates interfaces that facilitate ionic exchanges between the external medium and the interior of the blend of polymers wherein the carboxyl end groups were neutralized and the autocatalytic effect eliminated thereby resulting in a blend that was degraded homogeneously.

Another compound known to slow degradation of polymers, which is useful as a buffer 95 for the medical device 50 of the present invention, is caffeine. Polymer devices highly loaded with caffeine reduce degradation due to neutralization of carboxyl end groups while caffeine-free polymer implants exhibit accelerated degradation due to autocatalysis.

The degradation of polymers, such as PLA and PGA polymers, in the presence of basic compounds such as those mentioned above depend on parameters such as base catalysis, neutralization of carboxyl end groups, porosity, device dimensions, load and morphology of incorporated compounds.

Other influences on degradation of a polymer implant include molecular weight (MW). Accordingly, the higher the MW of a polymer, the lower the carboxyl end group concentration, and therefore, the slower the degradation (at the earlier stages). However, the presence of cyclic or acyclic monomers and oligomers in a polymer matrix can result in a rapid degradation of the polymer implant.

Moreover, the size and shape of the polymer implant 50 is also important. For example, very small polymer devices consisting of micro-particles, slim fibers or thin films degrade slower than larger sized polymer implants because autocatylitic degradation is reduced due to the easier diffusion of oligomers and neutralization of carboxyl end groups.

Gamma irradiation, such as through sterilization of medical devices, also has an effect on degradation of a polymer medical device implant. For instance, the gamma irradiation of Dexon® (Davis &Geck) and Vicryl® (Ethicon, Inc.) fibers results in an early pH fall of the degradation medium and a faster loss of tensile strength.

It will be appreciated by those skilled in the art that the relative amounts of the biodegradable and/or bioabsorbable material 75 to the biodegradable and/or bioabsorbable material 80 and relative amounts of the degradation additive 95 and/or drug 99 in the composites of the present invention will depend upon various parameters including, inter alia, the levels of strength, stiffness, and other physical and thermal properties, absorption and resorption rates, setting and hardening rates, deliverability, etc., which are required. The desired properties of the composites of the embodiments of the present invention and their level of requirement will depend upon the body structure area or anatomy where the medical device 50 and/or degradation additive 95 (and/or buffering agent and/or radiopaque agent and/or drug 99) is/are needed.

Figure 10:
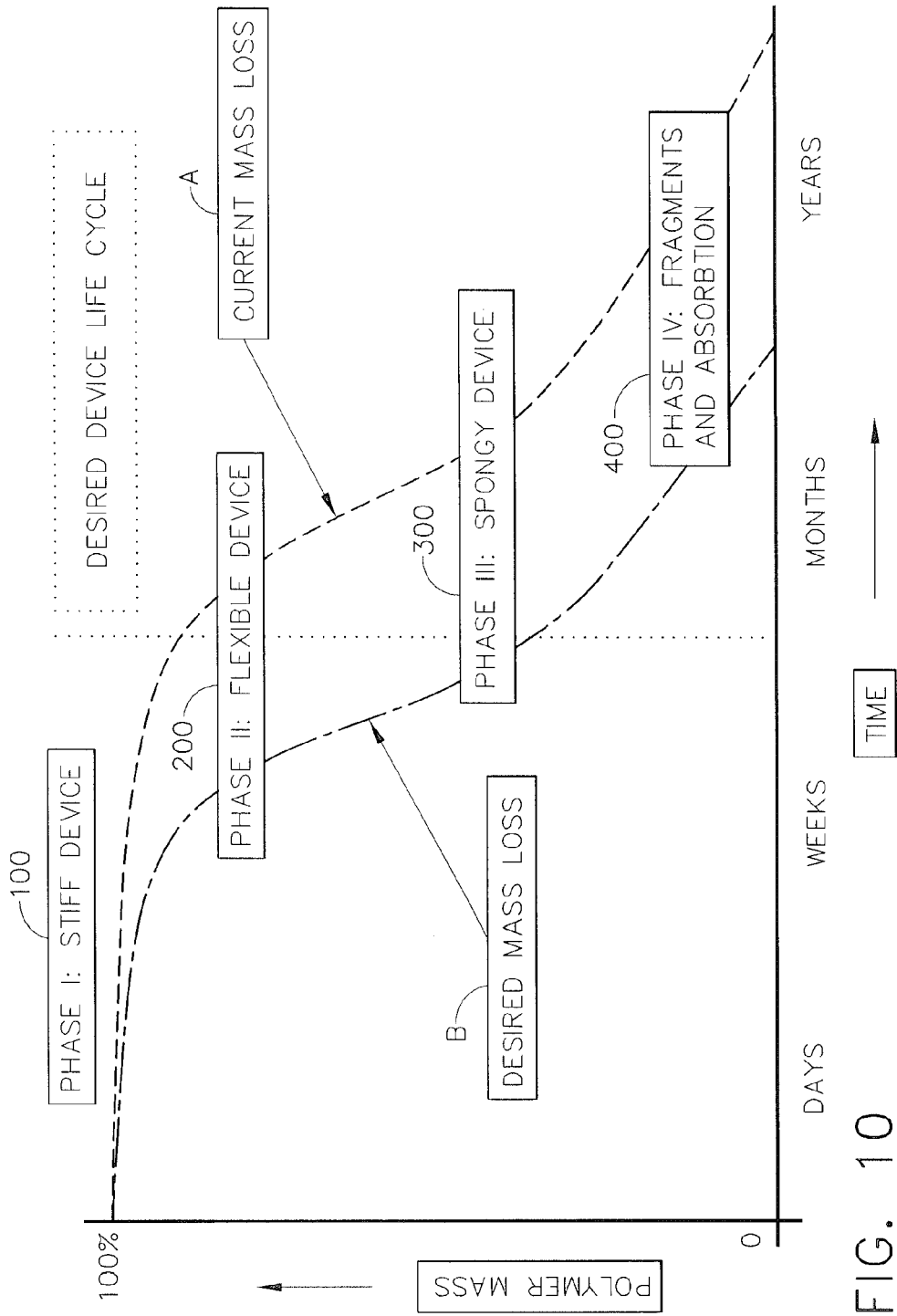
FIG. 10 is a graph schematically illustrating the different transition phases of degradation of the physical structure as a function of time for implantable biodegradable and/or bioabsorbable medical devices including comparisons of the current mass loss curve associated with known bioabsorbable medical implants versus the desired mass loss curve for an implantable biodegradable and/or bioabsorbable medical device associated with the present invention.

FIG. 10 is a graph schematically illustrating the different transition phases of degradation of the physical structure as a function of time for implantable biodegradable and/or bioabsorbable medical devices including comparisons of the current mass loss curve associated with known bioabsorbable medical implants versus the desired mass loss curve for an implantable biodegradable and/or bioabsorbable medical device 50 associated with the present invention.

As shown in FIG. 10, the different phases of an implanted biodegradable and/or bioabsorbable device during polymer degradation are physical states in which the polymer device exhibits different properties and/or characteristics. Additionally, the functional aspects for a given implantable bioabsorbable device (e.g., stent as on example for FIG. 10) is limited up to the transition of a device from being "stiff" or in a rigid state 100 (Phase T) to being "flexible" or in a flexible state 200 (Phase II) to transitioning to a "spongy" form or a spongy state or highly absorbent state 300 (Phase III) wherein the device loses the retention of physical properties to include transitioning to a fragmentation state 400 (Phase IV) whereby the device hydrolyses into fragments that are absorbed by the body. This process for known polymer medical device implants is schematically represented on the "current mass loss" curve designated by the letter A. Under these circumstances, the prior art polymer devices remain in place in the body until complete absorption even though it may not be required or desired in the body. This will prevent re-intervention at the site, if needed, and will limit treatment options available to the patients. This may also have a further inflammatory effect on the tissues associated with the implant, something that is avoided with the accelerated degradation process or desired mass curve (identified as letter B) of the present invention (medical device 50).

Thus, the degradation profile of the medical device 50 in accordance with the present invention follows the "desired mass loss" curve B. In this way, the medical device 50 is excreted from the body earlier (in less time) than the prior art polymer devices (as shown in curve B).

One example of the medical device 50 in use is for those embodiments whereby the device 50 is a stent utilizing a drug 99 for elution from polymer material of the stent (FIGS. 3, 5, 8 and 9) according to the desired mass loss curve B illustrated in FIG. 10. In this example (for all embodiments using a drug 99), the drug 99 is rapamycin. Rapamycin is a macrocyclic triene antibiotic produced by *Streptomyces hygroscopicus* as disclosed in U.S. Pat. No. 3,929,992. It has been found that rapamycin among other things inhibits the proliferation of vascular smooth muscle cells in vivo. Accordingly, rapamycin may be utilized in treating intimal smooth muscle cell hyperplasia, restenosis, and vascular occlusion in a mammal, particularly following either biologically or mechanically mediated vascular injury, or under conditions that would predispose a mammal to suffering such a vascular injury. Rapamycin functions to inhibit smooth muscle cell proliferation and does not interfere with the re-endothelialization of the vessel walls.

Rapamycin reduces vascular hyperplasia by antagonizing smooth muscle proliferation in response to mitogenic signals that are released during an angioplasty induced injury. Inhibition of growth factor and cytokine mediated smooth muscle proliferation at the late G1 phase of the cell cycle is believed to be the dominant mechanism of action of rapamycin. However, rapamycin is also known to prevent T-cell proliferation and differentiation when administered systemically. This is the basis for its immunosuppressive activity and its ability to prevent graft rejection.

As used herein, rapamycin includes rapamycin and all analogs, derivatives and conjugates that bind to FKBP12, and other immunophilins and possesses the same pharmacologic properties as rapamycin including inhibition of TOR.

Although the anti-proliferative effects of rapamycin may be achieved through systemic use, superior results may be achieved through the local delivery of the compound. Essentially, rapamycin works in the tissues, which are in proximity to the compound, and has diminished effect as the distance from the delivery device increases. In order to take advantage of this effect, one would want the rapamycin in direct contact with the lumen walls. Accordingly, in a preferred embodiment, the rapamycin is incorporated onto the surface of the stent or portions thereof. Essentially, the rapamycin is preferably incorporated into the stent 50 as described previously above and best illustrated in (FIGS. 3, 5, 8 and 9) where the stent 50 makes contact with the lumen wall of the vessel to be treated.

Rapamycin may be incorporated onto or affixed to the stent 50 in a number of ways. In exemplary embodiments, the rapamycin is directly incorporated into a polymeric matrix of the polymer materials 75 and/or 80 as described above. The rapamycin elutes from the polymeric matrix over time and enters the surrounding tissue. The rapamycin preferably remains on the stent for at least one (1) day up to approximately six (6) months, and more preferably between seven (7) days and sixty (60) days (i.e. a period of time ranging between 7 days to 60 days). Thus, these periods of time constitute the functional purpose or functional life or useful life for the stent 50 for these examples of the present invention.

Rapamycin functions to inhibit smooth muscle cell proliferation through a number of mechanisms. In addition, rapamycin reduces the other effects caused by vascular injury, for example, inflammation. The mechanisms of action and various functions of rapamycin are described in detail below. Rapamycin as used throughout this application shall include rapamycin, rapamycin analogs, derivatives and congeners that bind FKBP12 and possess the same pharmacologic properties as rapamycin, as described in detail below.

Rapamycin reduces vascular hyperplasia by antagonizing smooth muscle proliferation in response to mitogenic signals that are released during angioplasty. Inhibition of growth factor and cytokine mediated smooth muscle proliferation at the late G1 phase of the cell cycle is believed to be the dominant mechanism of action of rapamycin. However, rapamycin is also known to prevent T-cell proliferation and differentiation when administered systemically. This is the basis for its immunosuppressive activity and its ability to prevent graft rejection.

The molecular events that are responsible for the actions of rapamycin, a known anti-proliferative, which acts to reduce the magnitude and duration of neointimal hyperplasia, are still being elucidated. It is known, however, that rapamycin enters cells and binds to a high-affinity cytosolic protein called FKBP12. The complex of rapamycin and FKPB12 in turn binds to and inhibits a phosphoinositide (PI)-3 kinase called the "mammalian Target of Rapamycin" or TOR. TOR is a protein kinase that plays a key role in mediating the downstream signaling events associated with mitogenic growth factors and cytokines in smooth muscle cells and T lymphocytes. These events include phosphorylation of p27, phosphorylation of p70 s6 kinase and phosphorylation of 4BP-1, an important regulator of protein translation.

It is recognized that rapamycin reduces restenosis by inhibiting neointimal hyperplasia. However, there is evidence that rapamycin may also inhibit the other major component of restenosis, namely, negative remodeling. Remodeling is a process whose mechanism is not clearly understood but which results in shrinkage of the external elastic lamina and reduction in lumenal area over time, generally a period of approximately three to six months in humans.

Negative or constrictive vascular remodeling may be quantified angiographically as the percent diameter stenosis at the lesion site where there is no stent to obstruct the process. If late lumen loss is abolished in-lesion, it may be inferred that negative remodeling has been inhibited. Another method of determining the degree of remodeling involves measuring in-lesion external elastic lamina area using intravascular ultrasound (IVUS). Intravascular ultrasound is a technique that can image the external elastic lamina as well as the vascular lumen. Changes in the external elastic lamina proximal and distal to the stent from the post-procedural timepoint to four-month and twelve-month follow-ups are reflective of remodeling changes.

Evidence that rapamycin exerts an effect on remodeling comes from human implant studies with rapamycin coated stents showing a very low degree of restenosis in-lesion as well as in-stent. In-lesion parameters are usually measured approximately five millimeters on either side of the stent i.e. proximal and distal. Since the stent is not present to control remodeling in these zones which are still affected by balloon expansion, it may be inferred that rapamycin is preventing vascular remodeling.

The data in Table 1 below illustrate that in-lesion percent diameter stenosis remains low in the rapamycin treated groups, even at twelve months. Accordingly, these results support the hypothesis that rapamycin reduces remodeling.

TABLE 1.0

Angiographic In-Lesion Percent Diameter Stenosis (%), mean ± SD and "n =") In Patients Who Received a Rapamycin-Coated Stent

| Coating Group | Post Placement | 4-6 month Follow Up | 12 month Follow Up |
|---|---|---|---|
| Brazil | 10.6 ± 5.7 (30) | 13.6 ± 8.6 (30) | 22.3 ± 7.2 (15) |
| Netherlands | 14.7 ± 8.8 | 22.4 ± 6.4 | — |

Additional evidence supporting a reduction in negative remodeling with rapamycin comes from intravascular ultrasound data that was obtained from a first-in-man clinical program as illustrated in Table 2 below.

TABLE 2.0

Matched IVUS data in Patients Who Received a Rapamycin-Coated Stent

| IVUS Parameter | Post (n =) | 4-Month Follow-Up (n =) | 12-Month Follow-Up (n =) |
|---|---|---|---|
| Mean proximal vessel area ($mm^2$) | 16.53 ± 3.53 (27) | 16.31 ± 4.36 (28) | 13.96 ± 2.26 (13) |
| Mean distal vessel area ($mm^2$) | 13.12 ± 3.68 (26) | 13.53 ± 4.17 (26) | 12.49 ± 3.25 (14) |

The data illustrated that there is minimal loss of vessel area proximally or distally which indicates that inhibition of negative remodeling has occurred in vessels treated with rapamycin-coated stents.

Other than the stent itself, there have been no effective solutions to the problem of vascular remodeling. Accordingly, rapamycin may represent a biological approach to controlling the vascular remodeling phenomenon.

It may be hypothesized that rapamycin acts to reduce negative remodeling in several ways. By specifically blocking the proliferation of fibroblasts in the vascular wall in response to injury, rapamycin may reduce the formation of vascular scar tissue. Rapamycin may also affect the translation of key proteins involved in collagen formation or metabolism.

Rapamycin used in this context includes rapamycin and all analogs, derivatives and congeners that bind FKBP12 and possess the same pharmacologic properties as rapamycin.

In a preferred embodiment, the rapamycin is delivered by a local delivery device to control negative remodeling of an arterial segment after balloon angioplasty as a means of reducing or preventing restenosis. While any delivery device may be utilized, it is preferred that the delivery device comprises a biodegradable and/or bioabsorbable stent 50 that elutes or releases rapamycin such as those embodiments illustrated in FIGS. 3, 5, 8 and 9 and described previously above.

Data generated in porcine and rabbit models show that the release of rapamycin into the vascular wall from drug eluting stents in a range of doses (35-430 ug/15-18 mm coronary stent) produces a peak fifty to fifty-five percent reduction in neointimal hyperplasia. This reduction, which is maximal at about twenty-eight to thirty days, is typically not sustained in the range of ninety to one hundred eighty days in the porcine model.

Rapamycin produces an unexpected benefit in humans when delivered from a stent by causing a profound reduction in in-stent neointimal hyperplasia that is sustained for at least one year. The magnitude and duration of this benefit in humans is not predicted from animal model data. Rapamycin used in this context includes rapamycin and all analogs, derivatives and congeners that bind FKBP12 and possess the same pharmacologic properties as rapamycin.

As stated above, rapamycin reduces vascular hyperplasia by antagonizing smooth muscle proliferation in response to mitogenic signals that are released during angioplasty injury. Also, it is known that rapamycin prevents T-cell proliferation and differentiation when administered systemically. It has also been determined that rapamycin exerts a local inflammatory effect in the vessel wall when administered from a stent in low doses for a sustained period of time (approximately two to six weeks). The local anti-inflammatory benefit is profound and unexpected. In combination with the smooth muscle anti-proliferative effect, this dual mode of action of rapamycin may be responsible for its exceptional efficacy.

Accordingly, rapamycin delivered from a local device platform, reduces neointimal hyperplasia by a combination of anti-inflammatory and smooth muscle anti-proliferative effects. Rapamycin used in this context means rapamycin and all analogs, derivatives and congeners that bind FKBP12 and possess the same pharmacologic properties as rapamycin.

Rapamycin has also been found to reduce cytokine levels in vascular tissue when delivered from a stent. Data has shown that rapamycin is highly effective in reducing monocyte chemotactic protein (MCP-1) levels in the vascular wall. MCP-1 is an example of a proinflammatory/chemotactic cytokine that is elaborated during vessel injury. Reduction in MCP-1 illustrates the beneficial effect of rapamycin in reducing the expression of proinflammatory mediators and contributing to the anti-inflammatory effect of rapamycin delivered locally from a stent. It is recognized that vascular inflammation in response to injury is a major contributor to the development of neointimal hyperplasia.

Since rapamycin may be shown to inhibit local inflammatory events in the vessel it is believed that this could explain the unexpected superiority of rapamycin in inhibiting neointima.

As set forth above, rapamycin functions on a number of levels to produce such desired effects as the prevention of T-cell proliferation, the inhibition of negative remodeling, the reduction of inflammation, and the prevention of smooth muscle cell proliferation. While the exact mechanisms of these functions are not completely known, the mechanisms that have been identified may be expanded upon.

Studies with rapamycin suggest that the prevention of smooth muscle cell proliferation by blockade of the cell cycle is a valid strategy for reducing neointimal hyperplasia. Dramatic and sustained reductions in late lumen loss and neointimal plaque volume have been observed in patients receiving rapamycin delivered locally from a stent. The present invention expands upon the mechanism of rapamycin to include additional approaches to inhibit the cell cycle and reduce neointimal hyperplasia without producing toxicity.

The cell cycle is a tightly controlled biochemical cascade of events that regulate the process of cell replication. When cells are stimulated by appropriate growth factors, they move from $G_0$ (quiescence) to the G1 phase of the cell cycle. Selective inhibition of the cell cycle in the G1 phase, prior to DNA replication (S phase), may offer therapeutic advantages of cell preservation and viability while retaining anti-proliferative efficacy when compared to therapeutics that act later in the cell cycle i.e. at S, G2 or M phase.

Accordingly, the prevention of intimal hyperplasia in blood vessels and other conduit vessels in the body may be achieved using cell cycle inhibitors that act selectively at the G1 phase of the cell cycle. These inhibitors of the G1 phase of the cell cycle may be small molecules, peptides, proteins, oligonucleotides or DNA sequences. More specifically, these drugs or agents include inhibitors of cyclin dependent kinases (cdk's) involved with the progression of the cell cycle through the G1 phase, in particular cdk2 and cdk4.

Examples of drugs 99 that act selectively at the G1 phase of the cell cycle include small molecules such as flavopiridol and its structural analogs that have been found to inhibit cell cycle in the late G1 phase by antagonism of cyclin dependent kinases. Therapeutic agents that elevate an endogenous kinase inhibitory protein$^{kip}$ called P27, sometimes referred to as P27$^{kip1}$, that selectively inhibits cyclin dependent kinases may be utilized. This includes small molecules, peptides and proteins that either block the degradation of P27 or enhance the cellular production of P27, including gene vectors that can transfact the gene to produce P27. Staurosporin and related small molecules that block the cell cycle by inhibiting protein kinases may be utilized. Protein kinase inhibitors, including the class of tyrphostins that selectively inhibit protein kinases to antagonize signal transduction in smooth muscle in response to a broad range of growth factors such as PDGF and FGF may also be utilized.

As set forth above, the complex of rapamycin and FKPB12 binds to and inhibits a phosphoinositide (PI)-3 kinase called the mammalian Target of Rapamycin or TOR. An antagonist of the catalytic activity of TOR, functioning as either an active site inhibitor or as an allosteric modulator, i.e. an indirect inhibitor that allosterically modulates, would mimic the actions of rapamycin but bypass the requirement for FKBP12. The potential advantages of a direct inhibitor of TOR include better tissue penetration and better physical/chemical stability. In addition, other potential advantages include greater selectivity and specificity of action due to the specificity of an antagonist for one of multiple isoforms of TOR that may exist in different tissues, and a potentially different spectrum of downstream effects leading to greater drug efficacy and/or safety.

In addition, the inhibitor may be formulated for fast-release or slow release from the medical device 50 of the present invention with the objective of maintaining the rapamycin or other drug, agent or compound in contact with target tissues for a period ranging from three days to eight weeks, i.e. the functional life or useful life for the medical device 50 in this example.

As stated previously, the implantation of a coronary stent in conjunction with balloon angioplasty is highly effective in treating acute vessel closure and may reduce the risk of restenosis. Intravascular ultrasound studies suggest that coronary stenting effectively prevents vessel constriction and that most of the late luminal loss after stent implantation is due to plaque growth, probably related to neointimal hyperplasia. The late luminal loss after coronary stenting is almost two times higher than that observed after conventional balloon angioplasty. Thus, inasmuch as stents prevent at least a portion of the restenosis process, the use of drugs, agents or compounds which prevent inflammation and proliferation, or prevent proliferation by multiple mechanisms, combined with a stent may provide the most efficacious treatment for post-angioplasty restenosis.

The polymers selected for the first biodegradable and/or bioabsorbable material 75 and the second biodegradable and/or bioabsorbable material 80 for some preferred embodiments of the medical device 50 of the present invention have been selected based on the properties generally outlined below. For example, polyglycolide (PGA), a fast degrading polymer, has been selected for the biodegradable and/or bioabsorbable material 75 for several embodiments of the present invention.

PGA is the simplest linear aliphatic polyester and was used to develop the first totally synthetic absorbable suture, marketed as Dexon in the 1960s by Davis and Geck, Inc. (Danbury, Conn.). Glycolide monomer is synthesized from the dimerization of glycolic acid. Ring-opening polymerization yields high-molecular-weight materials, with approximately 1-3% residual monomer present. PGA is highly crystalline (45-55%), with a high melting point (220-225° C.) and a glass-transition temperature of 35-40° C. Because of its high degree of crystallinity, it is not soluble in most organic solvents; the exceptions are highly fluorinated organics such as hexafluoroisopropanol. Fibers from PGA exhibit high strength and modulus and are too stiff to be used as sutures except in the form of braided material. Sutures of PGA lose about 50% of their strength after 2 weeks and 100% at 4 weeks, and are completely absorbed in 4-6 months. Glycolide has been copolymerized with other monomers to reduce the stiffness of the resulting fibers.

Polylactide (PLA) and poly-L-lactide (PLLA), a slow degrading polymer (when compared to degradation rates associated with PGA), have been selected for the biodegradable and/or bioabsorbable material 80 for several embodiments of the present invention. As known, lactide is the cyclic dimer of lactic acid that exists as two optical isomers, d and l. l-lactide is the naturally occurring isomer, and dl-lactide is the synthetic blend of d-lactide and l-lactide. The homopolymer of l-lactide (LPLA or PLLA) is a semicrystalline polymer. These types of materials exhibit high tensile strength and low elongation, and consequently have a high modulus that makes them more suitable for load-bearing applications such as in orthopedic fixation and sutures. Poly(dl-lactide) (DLPLA) is an amorphous polymer exhibiting a random distribution of both isomeric forms of lactic acid, and accordingly is unable to arrange into an organized crystalline structure. This material has lower tensile strength, higher elongation, and a much more rapid degradation time, making it more attractive as a drug delivery system. Poly(l-lactide) (PLLA) is about 37% crystalline, with a melting point of 175-178° C. and a glass-transition temperature of 60-65° C. The degradation time of LPLA (PLLA) is much slower than that of DLPLA, requiring more than 2 years to be completely absorbed. Copolymers of l-lactide and dl-lactide have been prepared to disrupt the crystallinity of l-lactide and accelerate the degradation process.

Poly(lactide-co-glycolide) [PLGA] copolymers can be formed to extend the range of homopolymer properties. Copolymers of glycolide with both l-lactide and dl-glycolide have been developed for both device and drug delivery applications. It is important to note that there is not a linear relationship between the copolymer composition and the mechanical and degradation properties of the materials. For example, a copolymer of 50% glycolide and 50% dl-lactide degrades faster than either homopolymer. Copolymers of l-lactide with 25-70% glycolide are amorphous due to the disruption of the regularity of the polymer chain by the other monomer. A copolymer of 90% glycolide and 10% l-lactide was developed by Ethicon as an absorbable suture material under the trade name Vicryl. It absorbs within 3-4 months but has a slightly longer strength-retention time.

Poly(dioxanone) can be prepared by ring-opening polymerization of p-dioxanone. This resulted in the first clinically tested monofilament synthetic suture, known as PDS (marketed by Ethicon). This material has approximately 55% crystallinity, with a glass-transition temperature of −10 to 0° C. The polymer should be processed at the lowest possible temperature to prevent depolymerization back to monomer. Poly(dioxanone) has demonstrated no acute or toxic effects on implantation. The monofilament loses 50% of its initial breaking strength after 3 weeks and is absorbed within 6 months, providing an advantage over other products for slow-healing wounds.

Poly(ϵ-caprolactone) can be prepared by ring-opening polymerization of ϵ-caprolactone which yields a semicrystalline polymer with a melting point of 59-64° C. and a glass-transition temperature of −60° C. The polymer has been regarded as tissue compatible and used as a biodegradable suture in Europe. Because the homopolymer has a degradation time on the order of 2 years, copolymers have been synthesized to accelerate the rate of bioabsorption. For example, copolymers of ϵ-caprolactone with dl-lactide have produced materials with more-rapid degradation rates. A block copolymer of ϵ-caprolactone with glycolide, offering reduced stiffness compared with pure PGA, is being sold as a monofilament suture by Ethicon, Inc. (Somerville, N.J.), under the trade name Monocryl.

The composites of the present invention can be manufactured in the following process as an example. The preformed polymers, i.e. the first biodegradable and/or bioabsorbable material 75 and the second biodegradable and/or bioabsorbable material 80 and the degradation additive 95 (or other additives) and optionally the drug 99 and any of its required excipients are individually charged into a conventional mixing vessel having a conventional mixing device mounted therein such as an impeller i.e. the polymer material 75 and the degradation additive 95 and drug 99 (if included) are first mixed forming encapsulated degradation additive 95 and drug 99 (if included). The biodegradable and/or bioabsorbable material polymer(s) 75 and the degradation additive 95 and optionally the drug 99 are mixed at a temperature suitable for the given polymers as is known in this field until uniformly dispersion is obtained in order to ensure that the degradation additive 95 and drug 99 when optionally included as part of the encapsulation by the biodegradable and/or bioabsorbable polymer 75 (FIGS. 6-9). Then, the mixture may be further processed by removing it from the mixing device, cooling to room temperature, grinding, and drying under pressures below atmospheric at elevated temperatures for a period of time. Typical encapsulation processes can be used which can include spray drying, coacervation, etc. Alternatively, encapsulation can be prepared by extruding, tray drying, drum drying or the like to form solids which are then ground to the desired particle size. The encapsulated degradation additive 95 and drug 99 (if included) is then mixed with the biodegradable and/or bioabsorbable material 80 using suitable temperatures and processes steps such as those mentioned above and below.

It is important to note that all processing techniques used for the present invention will be at sufficient temperatures that will not degrade the drug 99, the degradation additive 95, the polymer material 75 and the polymer material 80.

As mentioned above, articles such as the medical devices 50 themselves may be molded from the composites of the present invention by use of various conventional injection and extrusion processes and molding equipment equipped with dry nitrogen atmospheric chamber(s) at acceptable temperatures.

The composites of this invention can be melt processed by numerous conventional methods to prepare a vast array of useful devices 50. These materials can be injection or compression molded to make implantable, biodegradable and/or bioabsorbable medical and surgical devices, especially biodegradable and/or bioabsorbable vascular devices such as stents including drug eluting stents and biodegradable and/or bioabsorbable cardiovascular devices such as heart valves including heart valves that are capable of eluting drugs 99.

Alternatively, the composites can be extruded (melt or solution) to prepare fibers and films. The filaments thus produced may be spun as multifilament yarn, or meshes, knitted or woven, and formed by conventional molding techniques into reinforced devices 50 and utilized where it is desirable that the structure have high tensile strength and desirable levels of compliance and/or ductility. Useful embodiments include preformed valves or stents for areas where vessels and heart tissue including heart valves are have been or are easily damaged or surgically removed.

According to the systems and methods of the present invention, a drug delivery device comprised of polymeric, bioabsorbable materials may be made by any of a variety of processes. The processes used to prepare the drug delivery devices are preferably low temperature processes in order to minimize the degradation of drugs or other bio-active agents that are unstable at high temperatures and are incorporated into the matrix of bioabsorbable polymeric materials comprising the device. Processing methods may comprise forming the device from bioabsorbable polymeric materials via low temperature, solution-based processes using solvents as by, for example, fiber spinning, including dry and wet spinning, electrostatic fiber spinning, co-mingled fibers, solvent extraction, coating, wire-coating, hollow fiber and membrane spinning, spinning disk (thin films with uniform thickness), ink-jet printing (three dimensional printing and the like), lyophilization, extrusion and co-extrusion, supercritical fluids, solvent cast films, or solvent cast tubes. Alternately, the drug delivery devices may also be prepared by more conventional polymer processing methods in melt condition for drugs or agents that are stable at high temperature as by, for example, fiber spinning, extrusion, co-extrusion, injection molding, blow molding, pultrusion and compression molding. Alternately, drugs may also be incorporated in the drug delivery device by diffusion through the polymer matrix. This may be achieved by several methods such as swelling the device in a drug-enriched solution followed by high-pressure diffusion or by swelling and diffusing the drug in the device using supercritical fluids. Alternately, the drugs or agents may be sprayed, dipped, or coated onto the device after formation thereof from the bioabsorbable polymers. In either case, the polymer matrix, and drug or agent blend when provided, is then converted into a structure such as fibers, films, discs/rings or tubes, for example, that is thereafter further manipulated into various geometries or configurations as desired.

Different processes may provide different structures, geometries or configurations to the bioabsorbable polymer being processed. For example, tubes processed from rigid polymers tend to be very stiff, but may be very flexible when processed via electrostatic processing or lyophilization. In the former case, the tubes are solid, whereas in the latter case, the tubes are porous. Other processes provide additional geometries and structures that may include fibers, microfibers, thin and thick films, discs, foams, microspheres and even more intricate geometries or configurations. Melt or solution spun fibers, films and tubes may be further processed into different designs such as tubular, slide and lock, helical or otherwise by braiding and/or laser cutting. The differences in structures, geometries or configurations provided by the different processes are useful for preparing different drug delivery devices with desired dimensions, strengths, drug delivery and visualization characteristics. The fibers, films or tubes may be laser cut to a desired geometry or configuration such as in the shape of a stent. Other machining techniques may also be utilized Different processes may likewise alter the morphological characteristics of the bioabsorbable polymer being processed. For example, when dilute solutions of polymers are stirred rapidly, the polymers tend to exhibit polymer chains that are generally parallel to the overall axis of the structure. On the other hand, when a polymer solution or melt is sheared and quenched to a thermally stable condition, the polymer chains tend to elongate parallel to the shear direction. Still other morphological changes tend to occur according to other processing techniques. Such changes may include, for example, spherulite to fibril transformation, polymorphic crystal formation change, re-orientation of already formed crystalline lamellae, formation of oriented crystallites, orientation of amorphous polymer chains, crystallization, and/or combinations thereof.

In the case of a stent comprised of bioabsorbable polymeric materials formed by supercritical fluids, such as supercritical carbon dioxide, the supercritical fluids are used to lower processing temperatures during extrusion, molding or otherwise conventional processing techniques. Different structures, such as fibers, tubes, films, or foams, may be formed using the supercritical fluids, whereby the lower temperature processing that accompanies the supercritical fluids tends to minimize degradation of the drugs incorporated into the structures formed.

The bioabsorbable polymer materials comprising the drug delivery device according to the invention may include radiopaque additives added directly thereto during processing of the matrix of the bioabsorbable polymer materials to enhance the radiopacity of the device. The radiopaque additives may include inorganic fillers, such as barium sulfate, bismuth subcarbonate, bismuth oxides and/or iodine compounds. The radiopaque additives may instead include metal powders such as tantalum, tungsten or gold, or metal alloys having gold, platinum, iridium, palladium, rhodium, a combination thereof, or other materials known in the art. The particle size of the radiopaque materials may range from nanometers to microns, preferably from less than or equal to about 1 micron to about 5 microns, and the amount of radiopaque materials may range from 0-99 percent (wt percent).

Because the density of the radiopaque additives is typically very high where the radiopaque materials are distributed throughout the matrix of bioabsorbable materials, dispersion techniques are preferably employed to distribute the radiopaque additives throughout the bioabsorbable materials as desired. Such techniques include high shear mixing, surfactant and lubricant additions, viscosity control, surface modification of the additive, and other particle size, shape and distribution techniques. In this regard, it is noted that the radiopaque materials may be either uniformly distributed throughout the bioabsorbable materials of the device, or may be concentrated in sections of the device so as to appear as markers similar to as described above.

The amount of drugs or other agents incorporated within the drug delivery device according to the systems and methods of the present invention may range from about 0 to 99 percent (percent weight of the device). The drugs or other agents may be incorporated into the device in different ways. For example, the drugs or other agents may be coated onto the device after the device has been formed, wherein the coating is comprised of bioabsorbable polymers into which the drugs or other agents are incorporated. Alternately, the drugs or other agents may be incorporated into the matrix of bioabsorbable materials comprising the device. The drugs or agents incorporated into the matrix of bioabsorbable polymers may be in an amount the same as, or different than, the amount of drugs or agents provided in the coating techniques discussed earlier if desired. These various techniques of incorporating drugs or other agents into, or onto, the drug delivery device may also be combined to optimize performance of the device, and to help control the release of the drugs or other agents from the device.

Where the drug or agent is incorporated into the matrix of bioabsorbable polymers comprising the device, for example, the drug or agent will release by diffusion and during degradation of the device. The amount of drug or agent released by diffusion will tend to release for a longer period of time than occurs using coating techniques, and may often more effectively treat local and diffuse lesions or conditions thereof. For regional drug or agent delivery such diffusion release of the drugs or agents is effective as well. Polymer compositions and their diffusion and absorption characteristics will control drug elution profile for these devices. The drug release kinetics will be controlled by drug diffusion and polymer absorption. Initially, most of the drug will be released by diffusion from the device surfaces and bulk and will then gradually transition to drug release due to polymer absorption. There may be other factors that will also control drug release. If the polymer composition is from the same monomer units (e.g., lactide; glycolide), then the diffusion and absorption characteristics will be more uniform compared to polymers prepared from mixed monomers. Also, if there are layers of different polymers with different drug in each layer, then there will be more controlled release of drug from each layer. There is a possibility of drug present in the device until the polymer fully absorbs thus providing drug release throughout the device life cycle.

The drug delivery device according to the systems and methods of the present invention preferably retains its mechanical integrity during the active drug delivery phase of the device. After drug delivery is achieved, the structure of the device ideally disappears as a result of the bioabsorption of the materials comprising the device. The bioabsorbable materials comprising the drug delivery device are preferably biocompatible with the tissue in which the device is implanted such that tissue interaction with the device is minimized even after the device is deployed within the patient. Minimal inflammation of the tissue in which the device is deployed is likewise preferred even as degradation of the bioabsorbable materials of the device occurs. In order to provide multiple drug therapy, enriched or encapsulated drug particles or capsules may be incorporated in the polymer matrix. Some of these actives may provide different therapeutic benefits such as anti-inflammatory, anti-thrombotic; etc.

As described above, polymer stents may contain therapeutic agents as a coating, e.g. a surface modification. Alternatively, the therapeutic agents may be incorporated into the stent structure, e.g. a bulk modification that may not require a coating. For stents prepared from biostable and/or bioabsorbable polymers, the coating, if used, could be either biostable or bioabsorbable. However, as stated above, no coating may be necessary because the device itself is fabricated from a delivery depot. This embodiment offers a number of advantages. For example, higher concentrations of the therapeutic agent or agents may be achievable such as about >50 percent by weight. In addition, with higher concentrations of therapeutic agent or agents, regional drug delivery (>5 mm) is achievable for greater durations of time. This can treat different lesions such as diffused lesions, bifurcated lesions, small and tortuous vessels, and vulnerable plaque. These drug-loaded stents can be delivered by different delivery systems such balloon expandable; self-expandable or balloon assist self-expanding systems.

As mentioned above, the composites of the present invention may also be used to coat substrates, i.e. serve as a biodegradable and/or bioabsorbable polymer coating or a biodegradable and/or bioabsorbable drug eluting polymer coating, such as biocompatible substrates such as meshes, the various structural components and elements of medical devices, for example, the hoops, loops, flexible links or bridges or extensions of the stent 50 or the housing, flaps or other components of the heart valve 50, etc. The coatings or blends 70 would be made by utilizing liquid composites of the present invention which would then be applied to the substrate by conventional coating techniques such as dipping, spraying, brushing, roller coating, etc.

Additionally, the composites can be molded to form films which are particularly useful for those applications where a drug delivery matrix in tissue (e.g., growth factors) is desired, for example for achieving angiogenesis and/or myogenesis in cardiovascular tissue including the vessels, myocardium, endocardium and epicardium or pericardium of the heart.

Furthermore, the composites of the present invention can be formed into foams, with open or closed cells, which are useful for applications where a high rate of tissue ingrowth is required such as remodeling heart tissue for inducing myogenesis or angiogenesis for treatment of cardiovascular disease such as congestive hear failure (CHF) or ischemic heart disease.

In more detail, the surgical and medical uses of the filaments, films, foams, molded articles, and injectable devices of the present invention include, but are not necessarily limited to vessels or heart tissue. The medical device 50 in accordance with the present invention can also be used for devices such as clamps, screws, and plates; clips; staples; hooks, buttons, and snaps; preformed tissue substitutes such as prosthetics or grafts, injectable polymers; vertebrae discs; anchoring devices such as suture anchors; septal occlusion devices; injectable defect fillers; preformed defect fillers; bone waxes; cartilage replacements; spinal fixation devices; drug delivery devices; foams with open or closed cells, and others.

All embodiments of the present invention allow for all of the biodegradable and/or bioabsorbable material 75 and 80 respectively to be removed or eliminated from the body in a short period of time after the functional aspects of the device 50 have been achieved. Accordingly, the present invention allows for re-intervention of the same treatment site by the doctors to treat the diseased tissue (or organs) in many cases vessels (in the cases where the medical device 50 is a stent). Thus, the present invention also permits a programmable drug release of drug 99 from the device 50 (FIGS. 3, 5, 8 and 9).

Inasmuch as the foregoing specification comprises preferred embodiments of the invention, it is understood that variations and modifications may be made herein, in accordance with the inventive principles disclosed, without departing from the scope of the invention.

While preferred embodiments of the present invention have been shown and described herein, it will be obvious to those skilled in the art that such embodiments are provided by way of example only. Numerous variations, changes and substitutions will now occur to those skilled in the art without departing from the invention. Accordingly, it is intended that the invention be limited only by the spirit and scope of the appended claims.

What is claimed is:

1. A medical device formed from a first biodegradable and/or bioabsorbable material and a second biodegradable and/or bioabsorbable material, the medical device comprising: a structure made of the second biodegradable and/or bioabsorbable material, the structure having the first biodegradable and/or bioabsorbable material encapsulating a degradation additive incorporated into the second biodegradable and/or bioabsorbable material; wherein the first biodegradable and/or bioabsorbable material has a degradation rate that is faster than the degradation rate of the second biodegradable and/or bioabsorbable material, the structure experiencing a period of accelerated degradation upon release of the degradation additive following sufficient degradation of the first biodegradable and/or bioabsorbable material.

2. The medical device according to claim 1, wherein the time to complete degradation for the second biodegradable and/or bioabsorbable material is between 3 months and 48 months.

3. The medical device according to claim 2, wherein the time to complete degradation for the first biodegradable and/or bioabsorbable material is between 1 day and 3 months.

4. The medical device according to claim 3, wherein the second biodegradable and/or bioabsorbable material is selected from the group consisting of polylactide based polymers, polyglycolide based polymers, poly($\alpha$-hydroxy esters), poly(oxaesters), poly(oxaamides), poly(DTH carbonates), poly(arylates), poly(imino-carbonates), phosphorous containing polymers, poly(phosphoesters), poly(phosphazenes), poly(ethylene glycol) based block copolymers, polyalkanoates, poly(hydroxyvalerate) (HV) co-polymers, PLA/PGA copolymers (95/5, 85/15), PLA-PCL copolymers that have lower absorption time than PLLA, and copolymers and blends of the foregoing.

5. The medical device according to claim 3, wherein the second biodegradable and/or bioabsorbable material is selected from the group consisting of poly(lactic acid), poly(glycolic acid), poly(caprolactone), poly(p-dioxanone), poly(trimethylene carbonate), PLLA, poly(lactide/glycolide), poly(glycolide/caprolactone) (75/25), poly(glycolide/trimethylene carbonate), tyrosine derived poly amino acid, PEG-PLA, PEG-poly(propylene glycol), PEG-poly(butylene terephthalate), ($\alpha$.-malic acid), poly(ester amide), poly(hydroxybutyrate) (HB) and copolymers and blends of the foregoing.

6. The medical device according to claim 4, wherein the first biodegradable and/or bioabsorbable material is selected from the group consisting of poly($\alpha$-hydroxy esters), polyanhydrides, polyorthoesters (diketene acetal based polymers), phosphorous containing polymers, PGA/PLA (90/10), PGAIPCL (75/25, 50/50, 65/35), poly(p-dioxanone) and their derivatives that have longer absorption time than PGA, poly(ethylene glycol), citrate esters, and copolymers and blends of the foregoing.

7. The medical device according to claim 4, wherein the first biodegradable and/or bioabsorbable material is selected from the group consisting of poly(glycolic acid) (PGA), poly(fumaric acid-sebacic acid), poly(carboxyphenoxy hexane-sebacic acid), poly(imidesebacic acid) (50-50), poly(imide-carboxyphenoxy hexane) (33-67), tyrosine derived poly amino acid, PGAIPLA (90/10), PGAIPCL (75/25, 50/50, 65/35), poly(p-dioxanone), poly(ethylene glycol) and copolymers and blends of the foregoing.

8. The medical device according to claim 1, wherein the degradation additive is selected from the group consisting of lipase-type enzymes, microorganism-produced enzymes, *Amycolatopsis* type enzymes, and PHB depolymerases.

9. The medical device according to claim 1, wherein the degradation additive is selected from the group consisting of Proteinase K, Bromelain, R delemer lipase, *Rhizopus arrhizus* lipase and *Pseudomonase* lipase.

10. The medical device according to claim 1, further comprising at least one further additive together with one or both of the first biodegradable and/or bioabsorbable material and the second biodegradable and/or bioabsorbable material and wherein the at least one further additive comprises a buffering agent selected from the group consisting of bioactive glasses, ceramics, inorganic basic fillers, carbonated calcium phosphates, acid/base titrating compounds and amine monomers.

11. The medical device according to claim 1, further comprising at least one further additive together with one or both of the first biodegradable and/or bioabsorbable material and the second biodegradable and/or bioabsorbable material and wherein the at least one further additive comprises a buffering agent selected from the group consisting of calcium phosphate, inorganic coral, caffeine, calcium hydroxyapatite, carbonated apatite, tricalcium phosphate, calcium carbonate, sodium bicarbonate, magnesium hydroxide, and lactate dehydrogenase.

12. The medical device according to claim 1, further comprising at least one further additive together with one or both of the first biodegradable and/or bioabsorbable material and the second biodegradable and/or bioabsorbable material and wherein the at least one further additive comprises a radiopaque agent selected from the group consisting of inorganic fillers, bismuth oxides, iodine compounds, metal powders including tantalum, tungsten or gold, and metal alloys having gold, platinum, iridium, palladium, rhodium or a combination thereof.

13. The medical device according to claim 3, wherein the medical device comprises a stent.

* * * * *